US012774460B2

(12) United States Patent
Shoichet et al.

(10) Patent No.: US 12,774,460 B2
(45) Date of Patent: Oct. 27, 2026

(54) CHONDROITINASE ABC MUTANTS AND METHODS OF MANUFACTURE AND USE THEREOF

(71) Applicants: THE GOVERNING COUNCIL OF THE UNIVERSITY OF TORONTO, Toronto (CA); THE REGENTS OF THE UNIVERSITY OF CALIFORNIA; YEDA RESEARCH AND DEVELOPMENT CO. LTD., Rehovot (IL)

(72) Inventors: Molly S. Shoichet, Toronto (CA); Marian H. Hettiaratchi, Toronto (CA); Teresa R. O'Meara, Summerland, CA (US); Matthew J. O'Meara, Summerland, CA (US)

( * ) Notice: Subject to any disclaimer, the term of this patent is extended or adjusted under 35 U.S.C. 154(b) by 703 days.

(21) Appl. No.: 17/798,415

(22) PCT Filed: Feb. 10, 2021

(86) PCT No.: PCT/CA2021/050145
§ 371 (c)(1),
(2) Date: Aug. 9, 2022

(87) PCT Pub. No.: WO2021/159205
PCT Pub. Date: Aug. 19, 2021

(65) Prior Publication Data

US 2023/0091945 A1 Mar. 23, 2023

Related U.S. Application Data

(60) Provisional application No. 62/972,308, filed on Feb. 10, 2020.

(51) Int. Cl.
*C12N 9/88* (2006.01)
*A61K 38/51* (2006.01)
*C12N 15/62* (2006.01)

(52) U.S. Cl.
CPC ................ *C12N 9/88* (2013.01); *A61K 38/51* (2013.01); *C12N 15/62* (2013.01); *C12Y 402/02021* (2013.01)

(58) Field of Classification Search
CPC . C12N 9/88; C12N 15/62; C12N 9/96; A61K 38/51; C12Y 402/02021; C12Y 402/0202; G01N 2333/4722; A61P 25/28; A61P 35/00; A61P 25/00
See application file for complete search history.

(56) References Cited

U.S. PATENT DOCUMENTS

| | | | | |
|---|---|---|---|---|
| 6,001,630 | A | 12/1999 | Ichikawa et al. | |
| 7,105,334 | B2 | 9/2006 | Pojasek et al. | |
| 7,485,295 | B2 | 2/2009 | Caggiano et al. | |
| 7,507,570 | B2 * | 3/2009 | Prabhakar .............. | A61K 38/47 435/85 |
| 8,226,941 | B2 | 7/2012 | Caggiano et al. | |
| 8,338,119 | B2 | 12/2012 | Prabhakar et al. | |
| 9,498,539 | B2 | 11/2016 | Shoichet et al. | |
| 9,987,340 | B2 | 6/2018 | Caggiano et al. | |
| 2007/0009222 | A1 | 1/2007 | Caggiano et al. | |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Hettiaratchi et al., Local delivery of stabilized chondroitinase ABC degrades chondroitin sulfate proteoglycans in stroke-injured rat brains. J. Controlled Release, 2019, vol. 297: 14-25. (Year: 2019).*
Hettiaratchi et al., Reengineering biocatalysts: computational redesign of chondroitinase ABC improves efficacy and stbility. Sci. Adv., 2020, vol. 6: eabc378, pp. 1-9. (Year: 2020).*
Kheirollahi et al., Rigidifying flexible sites: an approach to improve stability of chondroitinase ABC I. Int. J. Biol. Macromol., 2017, vol. 97: 270-278 (Year: 2017).*
Kisselev L., Polypeptide release factors in prokaryotes and eukaryotes: same function, different structure. Structure, 2002, vol. 10: 8-9. (Year: 2002).*
Moradi et al., Investigating the structural and functional features of representative recombinants of chondroitinase ABC I. Enz. Microbial Technol., 2017, vol. 107: 64-71. (Year: 2017).*
Paksula et al., Affinity-based release of chondroitinase ABC from a modified methylcellulose hydrogel. J. Controlled Release, 2013, vol. 171: 11-26. (Year: 2013).*

(Continued)

*Primary Examiner* — Ganapathirama Raghu
(74) *Attorney, Agent, or Firm* — Lathrop GPM LLP; James H. Velema; Laura A. Labeots

(57) ABSTRACT

The present application provides a Chondroitinase ABC (ChABC) mutants. ChABC stimulates axonal regeneration by degrading the inhibitory chondroitin sulfate (CS) and dermatan sulfate (DS) proteoglycans in the glial scar that forms after traumatic injuries to the central nervous system (CNS). However, the therapeutic utility of this potent, fragile protein is severely limited by rapid aggregation at physiological temperature. To overcome this limitation, the ChABC mutants were engineered to at least 15 point mutations in domain 2 of the wild-type ChABC and/or at least 5 point mutations in domain 3 of the wild-type enzyme. These mutants exhibit improved stability over wild-type ChABC. The present application further provides method and compositions comprising the mutant ChABC for treating conditions associated with excess proteoglycan formation or conditions for which treatment is benefitted by degradation of proteoglycans, including CNS injuries, scarring and cancer.

20 Claims, 16 Drawing Sheets

Figure 1:
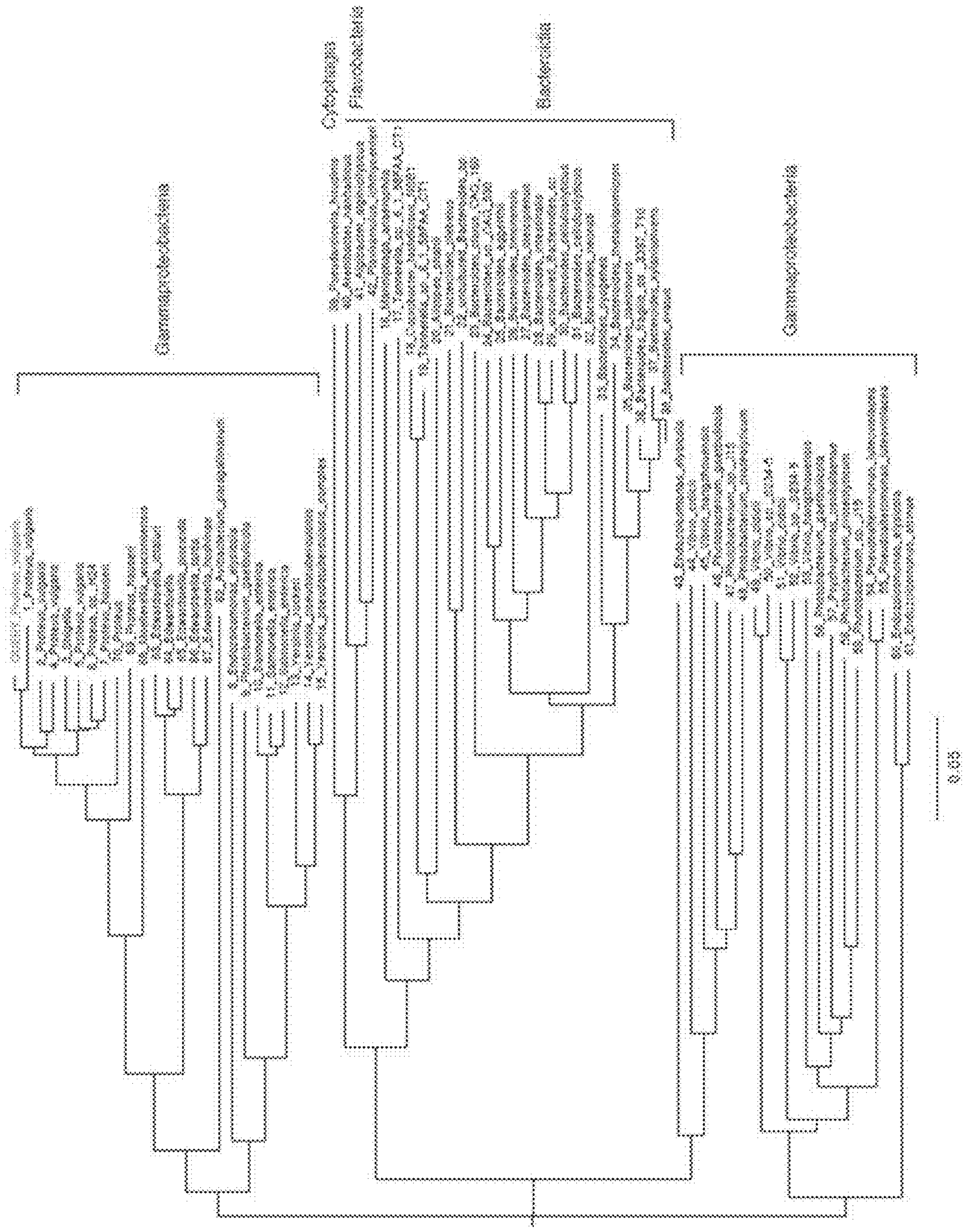

Specification includes a Sequence Listing.

(56) References Cited

OTHER PUBLICATIONS

Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Akanuma, et al., Experimental Evidence for the Thermophilicity of Ancestral Life. Proc. Natl. Acad. Sci. 2013, 110 (27), 11067-11072.
Askaripour, et al., Magnetite Nanoparticle as a Support for Stabilization of Chondroitinase ABCI. Artif. Cells Nanomedicine Biotechnol. 2019, 47 (1), 2721-2728. https://doi.org/10.1080/21691401.2019.1577879.
Bartlett, A. H .; Park, P. W. Proteoglycans in Host-Pathogen Interactions: Molecular Mechanisms and Therapeutic Implications. Expert Rev. Mol. Med. 2010, 12, e5. https://doi.org/10.1017/S1462399409001367.
Bodenhofer, et al., Msa: An R Package for Multiple Sequence Alignment. Bioinformatics 2015, btv494. https://doi.org/10.1093/bioinformatics/btv494.
Bradbury, et al., Chondroitinase ABC Promotes Functional Recovery after Spinal Cord Injury. Nature 2002, 416 (6881), 636.
Bradbury, et al., Manipulating the glial scar: Chondroitinase ABC as a therapy for spinal cord injury, Brain Research Bulletin, 2011, 84: 306-316.
Burnside, et al., Immune-evasive gene switch enables regulated delivery of chondroitinase after spinal cord injury. Brain 2018, 141 (8), 2362-2381. https://doi.org/10.1093/brain/awy158.
Chen, et al., Enzyme Activity Enhancement of Chondroitinase ABC I from Proteus Vulgaris by Site-Directed Mutagenesis. RSC Adv. 2015, 5 (93), 76040-76047. https://doi.org/10.1039/C5RA15220H.
Cleveland, et al., Smoothing by Local Regression: Principles and Methods. In Statistical theory and computational aspects of smoothing; Springer, 1996; pp. 10-49.
Corvetti, L.; Rossi, F. Degradation of Chondroitin Sulfate Proteoglycans Induces Sprouting of Intact Purkinje Axons in the Cerebellum of the Adult Rat. J. Neurosci. 2005, 25 (31), 7150-7158.
Ebinger, et al., Effects of Golden Hour Thrombolysis: A Prehospital Acute Neurological Treatment and Optimization of Medical Care in Stroke (PHANTOM-S) Substudy. JAMA Neurol. 2015, 72 (1), 25. https://doi.org/10.1001/jamaneurol.2014.3188.
Edgar, MUSCLE: Multiple Sequence Alignment with High Accuracy and High Throughput. Nucleic Acids Res. 2004, 32 (5), 1792-1797. https://doi.org/10.1093/nar/gkh340.
El-Gebali, et al., The Pfam Protein Families Database in 2019. Nucleic Acids Res. 2019, 47 (D1), D427-D432. https://doi.org/10.1093/nar/gky995.
Evaniew, et al., Methylprednisolone for the Treatment of Patients with Acute Spinal Cord Injuries: A Systematic Review and Meta-Analysis. J. Neurotrauma 2016, 33 (5), 468-481. https://doi.org/10.1089/neu.2015.4192.
Finn, et al., The Pfam Protein Families Database: Towards a More Sustainable Future. Nucleic Acids Res. 2016, 44 (D1), D279-D285. https://doi.org/10.1093/nar/gkv1344.
Fowler, et al., High-Resolution Mapping of Protein Sequence-Function Relationships. Nat. Methods 2010, 7 (9), 741-746. https://doi.org/10.1038/nmeth.1492.
Garcia, et al., Surface Proteoglycans as Mediators in Bacterial Pathogens Infections. Front. Microbiol. 2016, 7. https://doi.org/10.3389/fmicb.2016.00220.
García-Alías, et al., Chondroitinase ABC Treatment Opens a Window of Opportunity for Task-Specific Rehabilitation. Nat. Neurosci. 2009, 12 (9), 1145.
Gill, et al., Proteoglycans: Key Regulators of Pulmonary Inflammation and the Innate Immune Response to Lung Infection. Anat. Rec. Adv. Integr. Anat. Evol. Biol. 2010, 293 (6), 968-981. https://doi.org/10.1002/ar.21094.
Goldenzweig, et al., Automated Structure- and Sequence-Based Design of Proteins for High Bacterial Expression and Stability. Mol. Cell 2016, 63 (2), 337-346. https://doi.org/10.1016/j.molcel.2016.06.012.
Hamai, et al., Two Distinct Chondroitin Sulfate ABC Lyases: An Endoeliminase Yielding Tetrasaccharides and an Exoeliminase Preferentially Acting on Oligosaccharides. J. Biol. Chem. 1997, 272 (14), 9123-9130. https://doi.org/10.1074/jbc.272.14.9123.
Harris, et al., Chondroitinase ABC Enhances Pericontusion Axonal Sprouting But Does Not Confer Robust Improvements in Behavioral Recovery. J. Neurotrauma 2010, 27 (11), 1971-1982. https://doi.org/10.1089/neu.2010.1470.
Hettiaratchi, et al., Local Delivery of Stabilized Chondroitinase ABC Degrades Chondroitin Sulfate Proteoglycans in Stroke-Injured Rat Brains. J. Controlled Release 2019, 297, 14-25. https://doi.org/10.1016/j.jconrel.2019.01.033.
Hettiaratchi, et al., Reengineering biocatalysts: Computational redesign of Chondroitinase ABC improves efficacy and stability, Science Advances, 2020, 6: eabc6378.
Huang, et al., Crystal Structure of Proteus Vulgaris Chondroitin Sulfate ABC Lyase I at 1.9Å Resolution. J. Mol. Biol. 2003, 328 (3), 623-634. https://doi.org/10.1016/S0022-2836(03)00345-0.
International Search Report and Written Opinion for PCT International Patent Application No. PCT/CA2021/050145, mailed Apr. 19, 2021.
Kabsch, et al., Dictionary of Protein Secondary Structure: Pattern Recognition of Hydrogen-Bonded and Geometrical Features. Biopolymers 1983, 22 (12), 2577-2637. https://doi.org/10.1002/bip.360221211.
Kamisetty, et al., Assessing the Utility of Coevolution-Based Residue-Residue Contact Predictions in a Sequence-and Structure-Rich Era. Proc. Natl. Acad. Sci. 2013, 110 (39), 15674-15679.
Kheirollahi, et al., Investigating the Role of Loop 131-140 in Activity and Thermal Stability of Chondroitinase ABC I. Int. J. Biol. Macromol. 2018, 116, 811-816. https://doi.org/10.1016/j.ijbiomac.2018.05.094.
Kheirollahi, et al., Rigidifying Flexible Sites: An Approach to Improve Stability of Chondroitinase ABC I. Int. J. Biol. Macromol. 2017, 97, 270-278. https://doi.org/10.1016/j.ijbiomac.2017.01.027.
Kimura, On Some Principles Governing Molecular Evolution. Proc. Natl. Acad. Sci. 1974, 71 (7), 2848-2852.
Lee, et al., Sustained Delivery of Thermostabilized ChABC Enhances Axonal Sprouting and Functional Recovery after Spinal Cord Injury. Proc. Natl. Acad. Sci. 2010, 107 (8), 3340-3345. https://doi.org/10.1073/pnas.0905437106.
Lehmann, et al., The Consensus Concept for Thermostability Engineering of Proteins. Biochim. Biophys. Acta BBA—Protein Struct. Mol. Enzymol. 2000, 1543 (2), 408-415. https://doi.org/10.1016/S0167-4838(00)00238-7.
Li, et al., H. Roles of Chondroitin Sulfate and Dermatan Sulfate in the Formation of a Lesion Scar and Axonal Regeneration after Traumatic Injury of the Mouse Brain. J. Neurotrauma 2013, 30 (5), 413-425. https://doi.org/10.1089/neu.2012.2513.
Lin, et al., Chondroitinase ABC Has a Long-Lasting Effect on Chondroitin Sulphate Glycosaminoglycan Content in the Injured Rat Brain. J. Neurochem. 2007, 0 (0), 071116233414006-??? https://doi.org/10.1111/j.1471-4159.2007.05066.x.
Loladze, et al., Engineering a Thermostable Protein via Optimization of Charge-Charge Interactions on the Protein Surface †. Biochemistry 1999, 38 (50), 16419-16423. https://doi.org/10.1021/bi992271w.
Madeira, et al., The EMBL-EBI Search and Sequence Analysis Tools APIs in 2019. Nucleic Acids Res. 2019, 47 (W1), W636-W641. https://doi.org/10.1093/nar/gkz268.
Maleki, M, et al., Role of His-His Interaction in Ser474-His475-Tyr476 Sequence of Chondroitinase ABC I in the Enzyme Activity and Stability. Int. J. Biol. Macromol. 2018, 109, 941-949. https://doi.org/10.1016/j.ijbiomac.2017.11.075.
Matthews, et al., Enhanced Protein Thermostability from Site-Directed Mutations That Decrease the Entropy of Unfolding. Proc. Natl. Acad. Sci. 1987, 84 (19), 6663-6667. https:/doi.org/10.1073/pnas.84.19.6663.

(56) References Cited

OTHER PUBLICATIONS

Michel, et al., The Structure of Chondroitin B Lyase Complexed with Glycosaminoglycan Oligosaccharides Unravels a Calcium-Dependent Catalytic Machinery. J. Biol. Chem. 2004, 279 (31), 32882-32896. https://doi.org/10.1074/jbc.M403421200.
Mohammadyari, et al., Designing and Construction of Novel Variants of Chondroitinase ABC I to Reduce Aggregation Rate. Arch. Biochem. Biophys. 2019, 668, 46-53. https://doi.org/10.1016/j.abb.2019.05.013.
Moradi, et al., Investigating the Structural and Functional Features of Representative Recombinants of Chondroitinase Abc I. Enzyme Microb. Technol. 2017, 107, 64-71. https://doi.org/10.1016/j.enzmictec.2017.08.006.
Muir, et al., Recent Advances in the Therapeutic uses of Chondroitinase ABC, Experimental Neurology, 2019, 321: 113032.
Musil, et al., Computational Design of Stable and Soluble Biocatalysts. ACS Catal. 2019, 9 (2), 1033-1054. https://doi.org/10.1021/acscatal.8b03613.
Naderi, et al., Improving the Stability of Chondroitinase ABC I via Interaction with Gold Nanorods. Int. J. Biol. Macromol. 2018, 107, 297-304. https://doi.org/10.1016/j.ijbiomac.2017.08.167.
Nazari-Robati, et al., Co-Solvent Mediated Thermal Stabilization of Chondroitinase ABC I Form Proteus Vulgaris. Int. J. Biol. Macromol. 2012, 50 (3), 487-492. https://doi.org/10.1016/j.ijbiomac.2012.01.009.
Nazari-Robati, et al., Enhancement of Thermal Stability of Chondroitinase ABC I by Site-Directed Mutagenesis: An Insight from Ramachandran Plot. Biochim. Biophys. Acta BBA—Proteins Proteomics 2013, 1834 (2), 479-486. https://doi.org/10.1016/j.bbapap.2012.11.002.
Nori, et al., Human Oligodendrogenic Neural Progenitor Cells Delivered with Chondroitinase ABC Facilitate Functional Repair of Chronic Spinal Cord Injury. Stem Cell Rep. 2018, 11 (6), 1433-1448. https://doi.org/10.1016/j.stemcr.2018.10.017.
Omidi-Ardali, et al., NΔ89 and CΔ274 Truncated Enzymes of Chondroitinase ABC I Regain More Imperturbable Microenvironments Around Structural Components in Comparison to Their Wild Type. Protein J. 2019, 38 (2), 151-159. https://doi.org/10.1007/s10930-019-09821-y.
Pakulska, et al., Affinity-Based Release of Chondroitinase ABC from a Modified Methylcellulose Hydrogel. J. Controlled Release 2013, 171 (1), 11-16. https://doi.org/10.1016/j.jconrel.2013.06.029.
Pakulska, et al., Local Delivery of Chondroitinase ABC with or without Stromal Cell-Derived Factor 1α Promotes Functional Repair in the Injured Rat Spinal Cord. Biomaterials 2017, 134, 13-21.
Prabhakar, et al., Chondroitinase ABC I from Proteus Vulgaris : Cloning, Recombinant Expression and Active Site Identification. Biochem. J. 2005, 386 (1), 103-112. https://doi.org/10.1042/BJ20041222.
Prabhakar, V.; Capila, I.; Raman, R.; Srinivasan, A.; Bosques, C. J.; Pojasek, K.; Wrick, M. A.; Sasisekharan, R. The Catalytic Machinery of Chondroitinase ABC I Utilizes a Calcium Coordination Strategy to Optimally Process Dermatan Sulfate †. Biochemistry 2006, 45 (37), 11130-11139. https://doi.org/10.1021/bi0605484.
Rambaut, FigTree v1. 4.2, a Graphical Viewer of Phylogenetic Trees. 2014. 2018.
Rosenzweig, et al., Chondroitinase Improves Anatomical and Functional Outcomes after Primate Spinal Cord Injury. Nat. Neurosci. 2019, 1.
Schrodinger, The PyMOL Molecular Graphics System. 2010. Version 2019, 1, r1.
Shahaboddin, et al., Establishment of Aromatic Pairs at the Surface of Chondroitinase ABC I: The Effect on Activity and Stability. Appl. Biochem. Biotechnol. 2018, 186 (2), 358-370. https://doi.org/10.1007/s12010-018-2741-3.
Shahaboddin, et al., Improvement of Activity and Stability of Chondroitinase ABC I by Introducing an Aromatic Cluster at the Surface of Protein. Enzyme Microb. Technol. 2017, 105, 38-44. https://doi.org/10.1016/j.enzmiclec.2017.06.004.
Shamsi, et al., Optimization of Conformational Stability and Catalytic Efficiency in Chondroitinase ABC I by Protein Engineering Methods. Eng. Life Sci. 2016, 16 (8), 690-696. https://doi.org/10.1002/elsc.201600034.
Shaya, et al., Composite Active Site of Chondroitin Lyase ABC Accepting Both Epimers of Uronic Acid. Glycobiology 2008, 18 (3), 270-277. https://doi.org/10.1093/glycob/cwn002.
Shirdel, et al., Critical Role of a Loop at C-Terminal Domain on the Conformational Stability and Catalytic Efficiency of Chondroitinase ABC I. Mol. Biotechnol. 2015, 57 (8), 727-734. https://doi.org/10.1007/s12033-015-9864-3.
Silver, et al., Regeneration beyond the Glial Scar. Nat. Rev. Neurosci. 2004, 5 (2), 146-156. https://doi.org/10.1038/nrn1326.
Soleman, et al., Delayed Treatment with Chondroitinase ABC Promotes Sensorimotor Recovery and Plasticity after Stroke in Aged Rats. Brain 2012, 135 (4), 1210-1223. https://doi.org/10.1093/brain/aws027.
Tennant, Thinking Outside the Brain: Structural Plasticity in the Spinal Cord Promotes Recovery from Cortical Stroke. Exp. Neurol. 2014, 254, 195-199. https://doi.org/10.1016/j.expneurol.2014.02.003.
Tester, et al., Effect of Body Temperature on Chondroitinase ABC's Ability to Cleave Chondroitin Sulfate Glycosaminoglycans. J. Neurosci. Res. 2007, 85 (5), 1110-1118. https://doi.org/10.1002/jnr.21199.
Vulic, et al., Tunable Growth Factor Delivery from Injectable Hydrogels for Tissue Engineering. J. Am. Chem. Soc. 2012, 134 (2), 882-885. https://doi.org/10.1021/ja210638x.
Warren, et al., Rapid and Robust Restoration of Breathing Long after Spinal Cord Injury. Nat. Commun. 2018, 9 (1), 4843. https://doi.org/10.1038/s41467-018-06937-0.
Whitehead, et al., Optimization of Affinity, Specificity and Function of Designed Influenza Inhibitors Using Deep Sequencing. Nat. Biotechnol. 2012, 30 (6), 543-548. https://doi.org/10.1038/nbt.2214.
Whitmore, et al., Dichroweb, an Online Server for Protein Secondary Structure Analyses from Circular Dichroism Spectroscopic Data. Nucleic Acids Res. 2004, 32 (Web Server), W668-W673. https://doi.org/10.1093/nar/gkh371.
Wickham, Ggplot2: Elegant Graphics for Data Analysis; Springer, 2016.
Yamagata, et al., Purification and Properties of Bacterial Chondroitinases and Chondrosulfatases. J. Biol. Chem. 1968, 243 (7), 1523-1535.
Zhao, et al., Directed Evolution Converts Subtilisin E into a Functional Equivalent of Thermitase. Protein Eng. Des. Sel. 1999, 12 (1), 47-53. https://doi.org/10.1093/protein/12.1.47.
Zhao, et al., Targeting Chondroitin Saulfate Glycosaminoglycans to Treat Cardiac Fibrosis in Pathological Remodeling, Circulation, 2018, 137: 2497-2513.
Zuo, et al., Degradation of Chondroitin Sulfate Proteoglycan Enhances the Neurite-Promoting Potential of Spinal Cord Tissue. Exp. Neurol. 1998, 154 (2), 654-662.
Hettiaratchi et al., Local Delivery of Stabilized Chondroitinase ABC Degrades Chondroitin Sulfate Proteoglycans in Stroke-injured Rat Brains, Journal of Controlled Release, Mar. 19, 2019, 297: 14-25.
Hettiaratchi et al., Reegineering Biocatalysts: Computational Redesign of Chondroitinase ABC Improves Efficacy and Stability, Science Advances, Aug. 19, 2020, 6(34): 1-9.
International Search Report & Written Opinion Received for PCT Application No. PCT/CA2021/050145, mailed Apr. 19, 2021.
Muir et al., Recent Advances in the Therapeutic Uses of Chondroitinase ABC, Experimental Neurology, Nov., 2019, 321(113032): 1-17.
Shirdel et al., Critical Role of Loop at C-Terminal Domain on the Conformational Stability and Catalytic Efficiency of Chondroitinase ABC I, Mol. Biotechnol., Aug. 2015, 57(8): 727-734.
Zhao et al., Targeting Chondroitin Sulfate Glycosaminoglycans to Treat Cardiac Fibrosis in Pathological Remodeling, Circulation, Jun. 5, 2018, 137(23): 2497-2513.

* cited by examiner

Figure 4C:
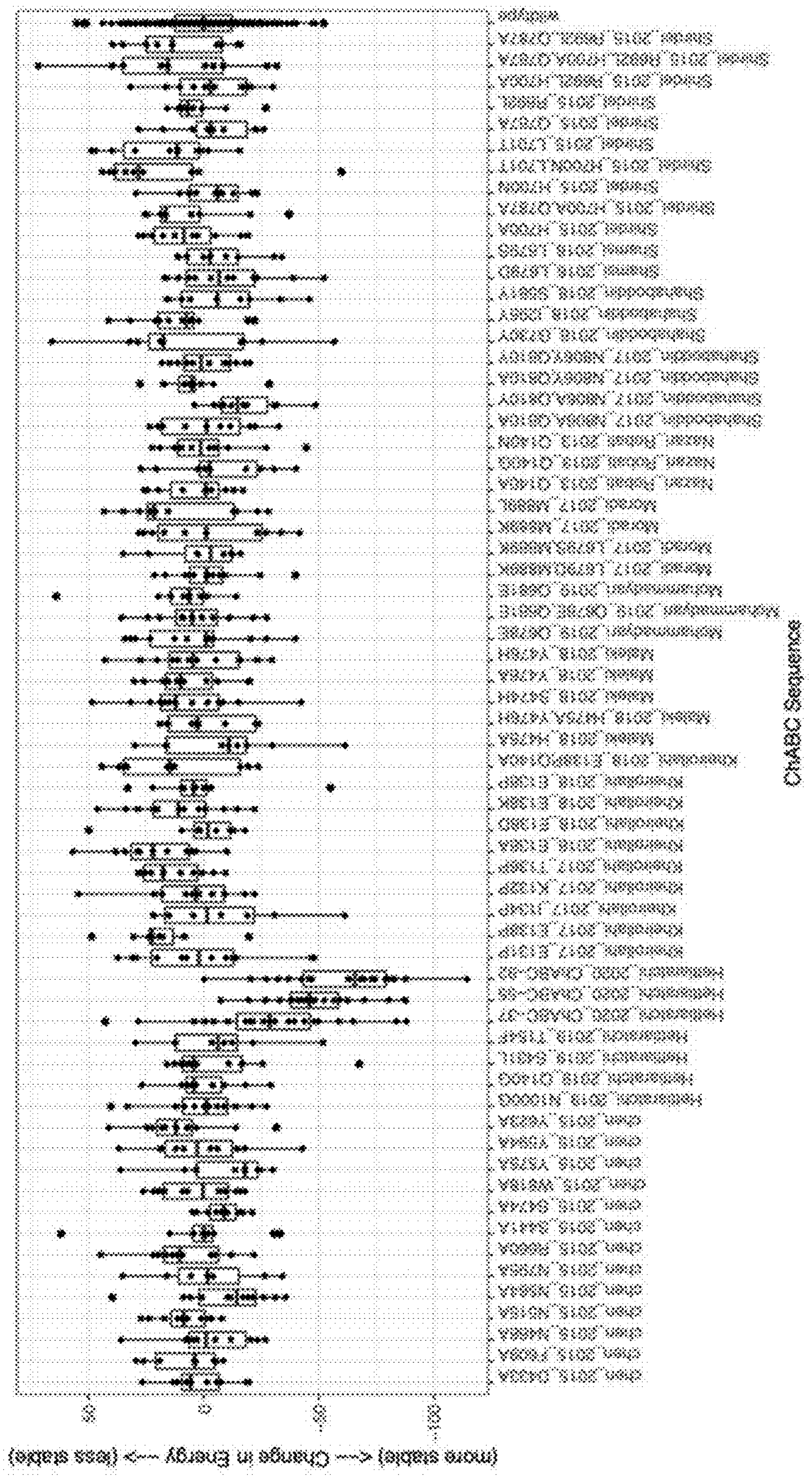

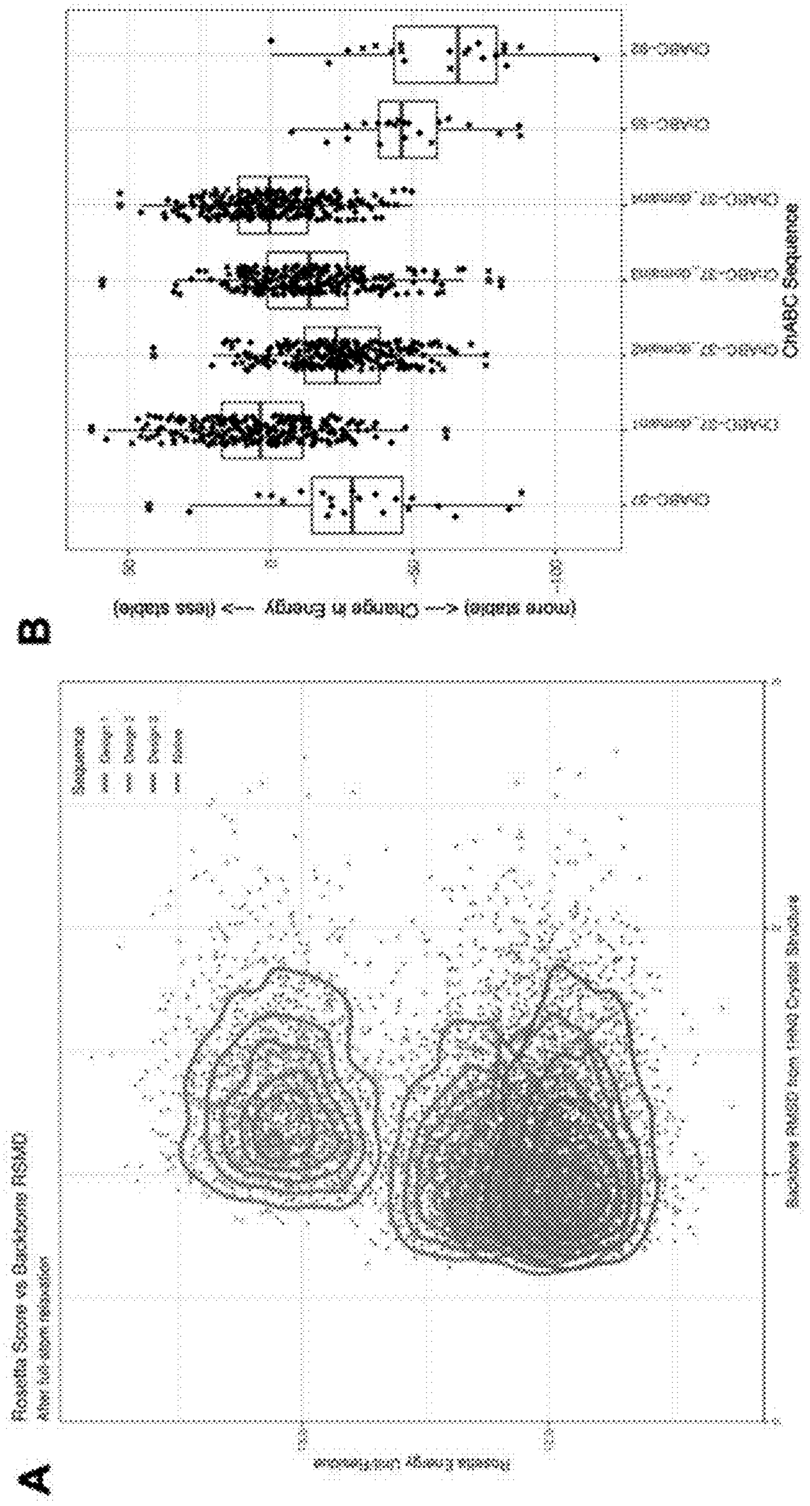
Figure 4A and B

SEQUENCE LISTING

```
<160> NUMBER OF SEQ ID NOS: 4

<210> SEQ ID NO 1
<211> LENGTH: 1021
<212> TYPE: PRT
<213> ORGANISM: Proteus vulgaris

<400> SEQUENCE: 1

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255
```

```
Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
        435                 440                 445

Leu Ser Arg Gln His Leu Ala Leu Leu Leu Leu Glu Pro Asp Asp Gln
    450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670
```

```
Val Ser Asn Gly Ser Gln Leu Ser Gln Gly Tyr Gln Gln Glu Gly Trp
        675                 680                 685

Asp Trp Asn Arg Met Glu Gly Ala Thr Thr Ile His Leu Pro Leu Lys
    690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe  Thr Ser Tyr
        995                 1000                 1005

Phe Gly  Ile Pro Gln Glu Ile  Lys Leu Ser Pro Leu  Pro
    1010                 1015                 1020
```

<210> SEQ ID NO 2
<211> LENGTH: 1021
<212> TYPE: PRT
<213> ORGANISM: Artificial Sequence
<220> FEATURE:
<223> OTHER INFORMATION: Mutant Chondroitinase ABC

<400> SEQUENCE: 2

```
Met Pro Ile Phe Arg Phe Thr Ala Leu Ala Met Thr Leu Gly Leu Leu
1               5                   10                  15
```

```
Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Tyr Ile Met Gly Asn Gln Ser Leu Gln Trp Lys Trp Lys
65                  70                  75                  80

Ala Gly Ser Ser Phe Thr Leu His Lys Pro Leu Ile Val Pro Thr Asp
                85                  90                  95

Lys Glu Ala Ser Lys Ala Trp Gly Arg Ser Ala Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Asn Ser Thr Ser Glu Ala Gln Ala Gly Phe Lys
    130                 135                 140

Val Lys Leu Asp Phe Thr Gly Trp Arg Ala Cys Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Tyr Ser Val Pro Glu Ile Gln Phe
225                 230                 235                 240

His Asn Val Glu Pro Gln Leu Pro Val Thr Pro Glu Asn Leu Ala Ala
                245                 250                 255

Val Asp Leu Ile Arg Gln Arg Leu Ile Asn Glu Phe Val Gly Gly Glu
            260                 265                 270

Lys Glu Thr Asn Leu Lys Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Ile Ile Thr Asp Lys Gln Lys Ile Ile Tyr Gln Pro Glu
305                 310                 315                 320

His Leu Asn Pro Gln Asp Lys Gln Leu Phe Asp Asn Tyr Val Ile Leu
                325                 330                 335

Gly Asp Tyr Thr Thr Leu Met Phe Asn Ile Ala Arg Ala Tyr Val Leu
            340                 345                 350

Asn Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Asn Ser Arg Trp Trp Tyr Ile Ser
385                 390                 395                 400

Ala Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Pro Asp Ser Ser Asp Leu Asp Tyr Phe Asn Thr
```

-continued

```
        435                 440                 445

Leu Ser Arg Gln His Leu Ala Leu Leu Leu Leu Glu Pro Asp Asp Gln
    450                 455                 460

Glu Arg Ile Asn Leu Leu His Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ala Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Pro Ser Ser Pro Asp Lys Thr Leu Ala Ser
            580                 585                 590

Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr His
                645                 650                 655

Lys Asp Asn Arg Tyr Gly Arg Tyr Gln Ser His Gly Val Ala Gln Ile
            660                 665                 670

Val Ser Tyr Gly Ser Gln Leu Ser Gln Gly Tyr Gln Glu Glu Gly Trp
        675                 680                 685

Asp Trp Asn Arg Met Pro Gly Ala Thr Thr Ile His Leu Pro Leu Asp
    690                 695                 700

Asp Leu Asp Ser Pro Lys Pro His Thr Leu Met Gln Arg Gly Glu Thr
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Glu Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860
```

```
Ser Thr Arg Pro Lys Asp Ala Ser Tyr Glu Tyr Met Val Phe Leu Asp
865                 870                 875                 880

Ala Thr Pro Glu Lys Met Gln Glu Tyr Ala Gln Lys Phe Arg Glu Asn
                885                 890                 895

Asn Arg Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe  Thr Ser Tyr
        995                 1000                1005

Phe Gly  Ile Pro Gln Glu Ile  Lys Leu Ser Pro Leu  Pro
    1010                1015                1020


<210> SEQ ID NO 3
<211> LENGTH: 1021
<212> TYPE: PRT
<213> ORGANISM: Artificial Sequence
<220> FEATURE:
<223> OTHER INFORMATION: Mutant Chondroitinase ABC

<400> SEQUENCE: 3

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Tyr Ile Met Gly Asn Gln Ser Leu Glu Trp Lys Trp Lys
65                  70                  75                  80

Ala Gly Ser Ser Phe Thr Leu His Lys Pro Leu Ile Val Pro Thr Asp
                85                  90                  95

Lys Glu Ala Ser Lys Ala Trp Gly Arg Ser Ala Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Asn Ser Thr Ser Glu Ala Gln Ala Gly Phe Lys
    130                 135                 140

Val Lys Leu Asp Phe Thr Gly Trp Arg Ala Ile Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Lys Gln Gly Arg Ile
        195                 200                 205
```

-continued

```
Phe Ile Asp Arg Ile Met Phe Ser Val Asp Asp Ala Arg Tyr Gln Trp
    210                 215                 220

Ser Asp Tyr Gln Val Lys Thr Arg Tyr Ser Val Pro Glu Ile Asp Phe
225                 230                 235                 240

His Asn Val Glu Pro Leu Leu Pro Ala Thr Pro Glu Asn Leu Ala Ala
                245                 250                 255

Val Asp Leu Ile Arg Gln Arg Leu Ile Asn Glu Phe Val Gly Gly Glu
            260                 265                 270

Lys Glu Thr Asn Leu Lys Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Ile Ile Thr Asp Lys Gln Lys Ile Ile Tyr Gln Pro Glu
305                 310                 315                 320

His Leu Asn Pro Gln Asp Lys Gln Leu Phe Asp Asn Tyr Val Ile Leu
                325                 330                 335

Gly Asp Tyr Thr Thr Leu Met Phe Asn Ile Ala Arg Ala Tyr Val Leu
            340                 345                 350

Asn Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Asn Ser Arg Trp Trp Tyr Ile Ser
385                 390                 395                 400

Ala Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Gly Pro Asp Ser Ser Asp Leu Asp Tyr Phe Asn Thr
        435                 440                 445

Leu Ser Arg Gln His Leu Ala Leu Leu Leu Leu Glu Pro Asp Asp Gln
    450                 455                 460

Glu Arg Ile Asn Leu Leu His Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ala Gln Leu Ile Tyr Leu Leu Arg Asp Thr Pro Phe
        515                 520                 525

Ser Val Gly Glu Ser Gly Trp Gln Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Pro Ser Ser Pro Asp Lys Thr Leu Ala Ser
            580                 585                 590

Ile Tyr Leu Arg Ile Ser Asp Lys Thr Gln Asn Glu Ser Glu Ala Ile
        595                 600                 605

Phe Gly Glu Thr Ile Thr Pro Ala Ser Leu Pro Gln Gly Phe Tyr Ala
    610                 615                 620
```

```
Phe Asn Gly Gly Ala Phe Gly Ile His Arg Trp Gln Asp Lys Met Val
625                 630                 635                 640

Thr Leu Lys Gly Tyr Asn Thr Asn Val Trp Ser Ser Glu Ile Tyr Thr
                645                 650                 655

Lys Asp Asn Arg Tyr Gly Arg Tyr Gln Ser His Gly Val Ala Gln Ile
            660                 665                 670

Val Ser Tyr Gly Ser Gln Leu Ser Gln Gly Tyr Gln Glu Glu Gly Trp
        675                 680                 685

Asp Trp Asn Arg Met Pro Gly Ala Thr Thr Ile His Leu Pro Leu Asp
    690                 695                 700

Asp Leu Asp Ser Pro Asn Pro His Thr Leu Met Gln Arg Gly Glu Thr
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Thr Met Pro Tyr Gln Thr Thr Leu Thr Gln Gly
                805                 810                 815

Asp Trp Leu Ile Asp Ser Asn Gly Asn Gly Tyr Leu Ile Thr Glu Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Ser Arg Arg Pro Lys Asp Ala Ser Tyr Glu Tyr Met Val Phe Leu Asp
865                 870                 875                 880

Ala Thr Pro Glu Lys Met Lys Glu Tyr Ala Gln Lys Phe Arg Glu Asn
                885                 890                 895

Asn Lys Leu Tyr Gln Val Leu Arg Lys Asp Lys Asp Val His Ile Ile
            900                 905                 910

Lys Asp Lys Leu Ser Asn Val Thr Gly Tyr Ala Phe Tyr Gln Pro Ala
        915                 920                 925

Glu Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe  Thr Ser Tyr
        995                 1000                1005

Phe Gly  Ile Pro Gln Glu Ile  Lys Leu Lys Pro Leu  Pro
    1010                1015                1020
```

<210> SEQ ID NO 4
<211> LENGTH: 1021
<212> TYPE: PRT

<213> ORGANISM: Artificial Sequence
<220> FEATURE:
<223> OTHER INFORMATION: Mutant Chondroitinase ABC

<400> SEQUENCE: 4

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Asn Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Tyr Ile Met Gly Asn Gln Ser Leu Glu Trp Lys Trp Lys
65                  70                  75                  80

Ala Gly Ser Ser Phe Val Leu His Lys Pro Leu Ile Ile Pro Thr Asp
                85                  90                  95

Lys Glu Ala Ser Lys Ala Trp Gly Arg Pro Ala Thr Pro Val Phe Ser
            100                 105                 110

Phe Trp Leu Tyr Asn Glu Lys Pro Ile Asp Gly Tyr Leu Arg Ile Asp
        115                 120                 125

Phe Gly Glu Lys Leu Asn Ser Thr Ser Glu Ala Gln Ala Gly Phe Lys
    130                 135                 140

Val Lys Leu Asn Phe Thr Gly Trp Arg Ala Cys Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Lys Gln Gly Arg Ile
        195                 200                 205

Phe Ile Asp Arg Ile Met Phe Ser Val Asp Asp Ala Arg Tyr Gln Trp
    210                 215                 220

Ser Asp Tyr Gln Val Lys Thr Arg Tyr Ser Val Pro Glu Ile Asp Phe
225                 230                 235                 240

His Asn Val Glu Pro Leu Pro Pro Val Thr Pro Glu Asn Leu Ala Ala
                245                 250                 255

Val Asp Thr Ile Arg Gln Arg Leu Ile Asp Glu Phe Ala Gly Gly Glu
            260                 265                 270

Lys Glu Thr Asn Leu Lys Leu Glu Glu Asn Ile Asp Lys Leu Lys Ser
        275                 280                 285

Lys Phe Asp Ala Leu Asn Ile His Thr Leu Ala Asp Gly Gly Thr Gln
    290                 295                 300

Gly Arg His Ile Ile Thr Asp Lys Gln Lys Ile Ile Tyr Gln Pro Glu
305                 310                 315                 320

His Leu Asn Ala Gln Asp Lys Gln Leu Phe Asp Asn Tyr Val Ile Leu
                325                 330                 335

Gly Asp Tyr Thr Thr Leu Met Phe Asn Ile Ala Arg Ala Tyr Tyr Leu
            340                 345                 350

Asn Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Asn Ser Arg Trp Trp Tyr Ile Ser

```
385                 390                 395                 400

Ala Leu Leu Met Ser Asp Ala Leu Lys Glu Ala Asn Leu Gln Gln Gln
                405                 410                 415

Val Tyr Asp Ser Leu Leu Trp Tyr Ser Arg Glu Phe Lys Ser Ser Phe
            420                 425                 430

Asp Met Lys Val Gly Pro Asp Ser Ser Asn Leu Asp Tyr Phe Asn Thr
        435                 440                 445

Leu Ser Arg Gln His Leu Ala Leu Leu Leu Leu Glu Pro Asp Asp Gln
    450                 455                 460

Glu Arg Ile Asn Leu Val His Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ala Gln Leu Ile Tyr Leu Leu Arg Asp Thr Pro Phe
        515                 520                 525

Glu Val Gly Glu Ser Gly Trp Gln Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Pro Ser Ser Pro Asp Lys Thr Leu Ala Ala
            580                 585                 590

Ile Tyr Leu Arg Ile Ser Gly Lys Thr Gln Asn Glu Ser Lys Ala Ile
        595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gly Asp Lys Met Val
625                 630                 635                 640

Thr Leu Lys Gly Tyr Asn Lys Asn Val Trp Ser Ser Glu Ile Tyr Thr
                645                 650                 655

Lys Asp Asn Arg Tyr Gly Arg Tyr Gln Ser His Gly Thr Ala Gln Ile
            660                 665                 670

Val Ser Tyr Gly Ser Gln Lys Ser Gln Gly Tyr Gln Glu Asn Gly Trp
        675                 680                 685

Asp Trp Asn Arg Met Pro Gly Ala Thr Thr Ile His Leu Pro Leu Glu
    690                 695                 700

Glu Leu Asp Ser Pro Asn Pro His Thr Leu Met Gln Arg Gly Glu Thr
705                 710                 715                 720

Gly Phe Ser Gly Thr Ser Ser Leu Glu Gly Gln Tyr Gly Met Met Ala
                725                 730                 735

Phe Asn Leu Gln Tyr Pro Gln Asn Leu Pro Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Tyr Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Thr Gln Met Pro Tyr Gln Thr Thr Leu Gly Gln Gly
                805                 810                 815
```

```
Asp Trp Leu Ile Asp Ser Asn Gly Asn Gly Tyr Leu Ile Thr Glu Ala
            820                 825                 830

Glu Lys Val Asn Val Ser Arg Gln His Gln Thr Ser Ala Asp Asn Lys
        835                 840                 845

Asn Arg Gln Pro Thr Glu Gly Asn Phe Ser Ser Ala Trp Ile Asp His
    850                 855                 860

Ser Arg Arg Pro Lys Asn Ala Ser Tyr Glu Tyr Met Val Phe Leu Asp
865                 870                 875                 880

Ala Thr Pro Glu Lys Met Lys Glu Tyr Ala Gln Lys Phe Arg Glu Asn
                885                 890                 895

Asn Lys Leu Tyr Gln Val Leu Arg Lys Asp Lys Asp Val His Ile Ile
            900                 905                 910

His Asp Lys Leu Ser Asn Val Thr Gly Tyr Ala Phe Tyr Gln Pro Ala
        915                 920                 925

Glu Ile Glu Asp Lys Trp Ile Lys Lys Val Asn Arg Pro Ala Ile Val
    930                 935                 940

Met Thr His Arg Gln Lys Asp Ile Leu Ile Val Ser Ala Ser Thr Pro
945                 950                 955                 960

Asp Leu Asn Met Thr Arg Gln Lys Ala Ala Lys Pro Val Thr Ile Asn
                965                 970                 975

Val Thr Ile Lys Gly Lys Trp Gln Ser Ala Asp Lys Asn Ser Glu Val
            980                 985                 990

Lys Tyr Gln Val Ser Gly Asp Asn  Thr Val Leu Thr Phe  Thr Ser Tyr
        995                 1000                 1005

Phe Gly  Ile Pro Gln Glu Ile  Lys Leu Lys Pro Leu  Pro
    1010                 1015                 1020
```

CHONDROITINASE ABC MUTANTS AND METHODS OF MANUFACTURE AND USE THEREOF

CROSS-REFERENCE TO RELATED APPLICATIONS

The present application is a 35 U.S.C. § 371 filing of International Patent Application No. PCT/CA2021/050145, filed Feb. 10, 2021, which claims priority to U.S. Provisional Patent Application No. 62/972,308, filed Feb. 10, 2020, which are hereby incorporated by reference in their entirety.

FIELD OF THE INVENTION

The present application pertains to the field of Chondroitinase ABC. More particularly, the present application relates to Chondroitinase ABC mutants, and methods of manufacture and therapeutic uses thereof.

INTRODUCTION

Reactive cellular processes following traumatic injury to the central nervous system (CNS) create a growth-inhibitory microenvironment that is challenging to repair. As an adaptive response to CNS injury, glial cells produce glycosaminoglycan (GAG) epimers of uronic acid[1] cross-linked with proteins to form a proteoglycan-rich glial scar, which protects the injury site from further damage caused by secondary injury mechanisms. Despite the importance of this glial scar in tissue protection immediately following injury, chondroitin sulfate (CS) and dermatan sulfate (DS) proteoglycans inhibit long-term axonal regrowth, causing severe loss of motor and sensory function for patients suffering from CNS injuries such as spinal cord injury and stroke.[2] Current treatments for CNS injury include tissue plasminogen activator to induce thrombolysis and enhance reperfusion after stroke[3] and methylprednisolone to reduce inflammation following spinal cord injury.[4] These treatment strategies have a limited timeframe for efficacy, reduce the injury rather than promote tissue regeneration, and have no impact on the inhibitory glial scar.

Proteoglycan deposition at injury sites limits microbial infection and the spread of injury. In response, bacteria have evolved enzymes to degrade proteoglycans as a nutrient source, facilitating adherence, colonization, and infection of animal tissues.[5-7] The enzyme chondroitinase ABC (ChABC) degrades both CS and DS proteoglycans through a unique dual endo- vs exo-lyase catalytic mechanism,[8,9] and is widely expressed by bacteria in human microbiomes, including gut and wound microbiomes.[9,10]

ChABC can also be harnessed as a therapeutic, to degrade CS and DS proteoglycans in glial scar following CNS injury, attenuate growth-inhibitory biochemical cues, and extend the time frame of recovery by promoting plasticity, axonal sprouting, and neuroprotection in animal models of spinal cord injury and stroke.[11-14] Importantly, there is evidence that delivery of ChABC—either on its own or in combination with other therapeutic agents—can stimulate recovery of sensorimotor function,[15-18] with recent studies progressing to primates.[19] However, despite progress in pre-clinical models of CNS injury, widespread application of ChABC is hindered by its instability at physiological temperature and pH, resulting in rapid unfolding, aggregation, and inactivation.[20] One strategy to address this drawback is to deliver repeated bolus injections of the protein[13,17] or use osmotic pumps for constant enzyme infusion.[21] These strategies are invasive and introduce risks of infection, especially as the protective scar tissue is degraded. Another strategy is local delivery by lentivirus or adeno associated virus (AAV)[21a]; however, viral delivery can cause inflammation and additional scarring in the CNS, limiting the utility of this therapeutic strategy. In addition, the expressed ChABC still suffers from instability. It is preferable to make use of a ChABC that is more stable and less susceptible to unfolding, aggregation and inactivation.

Several groups have had limited success engineering more stable versions of ChABC using a diversity of approaches that have had only marginal impact on stability, activity and functional half-life. These include introducing point mutations,[11,22-33] truncations,[34] formulations with different solvents,[35,36] tethering with poly(ethylene glycol) (PEG) chains,[11] and/or attachment to nanoparticles[37,38] (Table 1).

A need remains for a stable version of ChABC that retains activity for use in therapeutic applications.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide Chondroitinase ABC mutants and methods of manufacture and uses thereof.

The present application relates to chondroitinase ABC lyase I (ChABC) and uses thereof. In particular, the present application provides recombinant and mutated ChABC, and methods of manufacture and use thereof. The mutant ChABC enzymes of the present application are useful for a variety of purposes, including degrading and/or analyzing polysaccharides such as glycosaminoglycans (GAGs). These GAGs can include, but are not limited to, chondroitin sulfate, dermatan sulfate and heparin sulfate proteoglycans. The mutant ChABC enzymes can also be used in therapeutic methods for treating conditions associated with excess proteoglycan formation or conditions for which treatment is benefitted by degradation of proteoglycans, such as, but not limited to, promoting nerve regeneration, promoting stroke recovery, treating spinal cord injury, treating epithelial disease, treating infections, treating cancer, treating fibrosis, treating scars.

In accordance with an aspect of the present application, there is provided a mutant of a wild-type chondroitinase ABC (ChABC) having ChABC activity, a melting temperature that is at least 4° C. higher than the melting temperature of the wild-type ChABC and a functional half-life that is at least 4 times longer than that of the wild-type ChABC.

In accordance with another aspect of the present application, there is provided a mutant of a wild-type ChABC said mutant having ChABC activity, a melting temperature that is at least 4° C. higher than the melting temperature of the wild-type ChABC and a functional half-life that is at least 4 times longer than that of the wild-type ChABC, wherein the mutant comprises at least 15 point mutations in domain 2 of the wild-type ChABC and/or at least 5 point mutations in domain 3 of the wild-type enzyme.

In certain embodiments, the wild-type ChABC has the amino acid sequence of SEQ ID NO:1. In other embodiments the wild-type ChABC has an amino acid sequence that is homologous to the amino acid sequence of SEQ ID NO:1.

In certain embodiments, the mutant comprises the mutations in domain 2 are:

substitutions in the amino acid sequence of SEQ ID NO:1 selected from the group consisting of K244E, Q246L, L247P, V249A, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, V470L, N471H, S517A, S529E, N536Q, K583P, S592A, A596R, and D599G; or substitutions in the homologous amino acid sequence selected from the group consisting of substitutions corresponding with K244E, Q246L, L247P, V249A, 1257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, V470L, N471H, S517A, S529E, N536Q, K583P, S592A, A596R, and D599G in SEQ ID NO:1.

In certain embodiments, the mutant comprises the mutations in domain 3 are:

substitutions in the amino acid sequence of SEQ ID NO:1 selected from the group consisting of Q636G, A644G, T647K, N656T, N656H, V669T, N675Y, L679K, Q685E, Q686N, E694P, K704D, K704E, D705E, K710N, R720T, 1740Q, A743Q, E746P, K779Y, E805T, N806Q, N806T, Q814T, Q814G, Q831E, V843T, E846D, T866R and D870N; or substitutions in the homologous amino acid sequence selected from the group consisting of substitutions corresponding with Q636G, A644G, T647K, N656T, N656H, V669T, N675Y, L679K, Q685E, Q686N, E694P, K704D, K704E, D705E, K710N, R720T, 1740Q, A743Q, E746P, K779Y, E805T, N806Q, N806T, Q814T, Q814G, Q831E, V843T, E846D, T866R and D870N in SEQ ID NO:1.

Also provided is a nucleic acid molecule, vector and host cell encoding the mutant ChABC as described herein. Also provided are compositions comprising the mutant ChABC polypeptide, or nucleic acid molecule, vector and host cell, in vitro methods of use thereof for degradation or analysis of proteoglycans, and therapeutic methods and uses for promoting nerve regeneration, or treating a subject having a central nervous system injury, a spinal cord injury, a neurodegenerative disorder, cancer, a fibrosis disease (such as, cardiac fibrosis, pulmonary fibrosis, or fibrotic renal disease), scarring or having had a stroke.

BRIEF DESCRIPTION OF TABLES AND FIGURES

For a better understanding of the application as described herein, as well as other aspects and further features thereof, reference is made to the following description which is to be used in conjunction with the accompanying drawings, described briefly below.

FIG. 1: Dendrogram for ChABC sequences used to develop consensus design restraints. Protein sequences from the NCBI non-redundant database with BlastP E-value<1e-4 were aligned using MUSCLE™ and filtered for the absence of insertions or deletions in DSSP-labeled loops. This process identified 70 sequences. The multiple-sequence alignment is shown as a neighbor-joining tree without distance corrections computed using the clustalo[65] package and plotted using FigTree 1.4.41, with mid-point rooting labeled with the species and class.[20]

Figure 2:
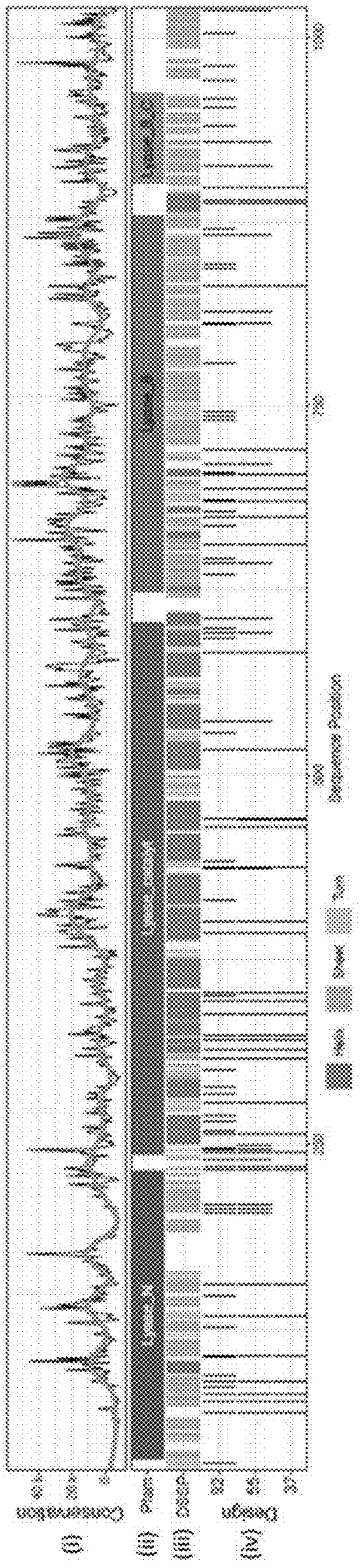

FIG. 2: Mutations introduced in ChABC sequence for designed proteins. Tracks include i) ChABC sequence conservation where lower values indicate more conserved, defined by the sum pairwise BLOSUM64 substitution scores across all pairs of amino acids across 71 bacterial sequences in a ClustalW alignment; ii) Pfam domains, iii) secondary structure based on DSSP (Define Secondary Structure of Proteins) algorithm, and iv) positions of mutations for ChABC-37-SH3, ChABC-55-SH3, and ChABC-92-SH3.

Figure 3:
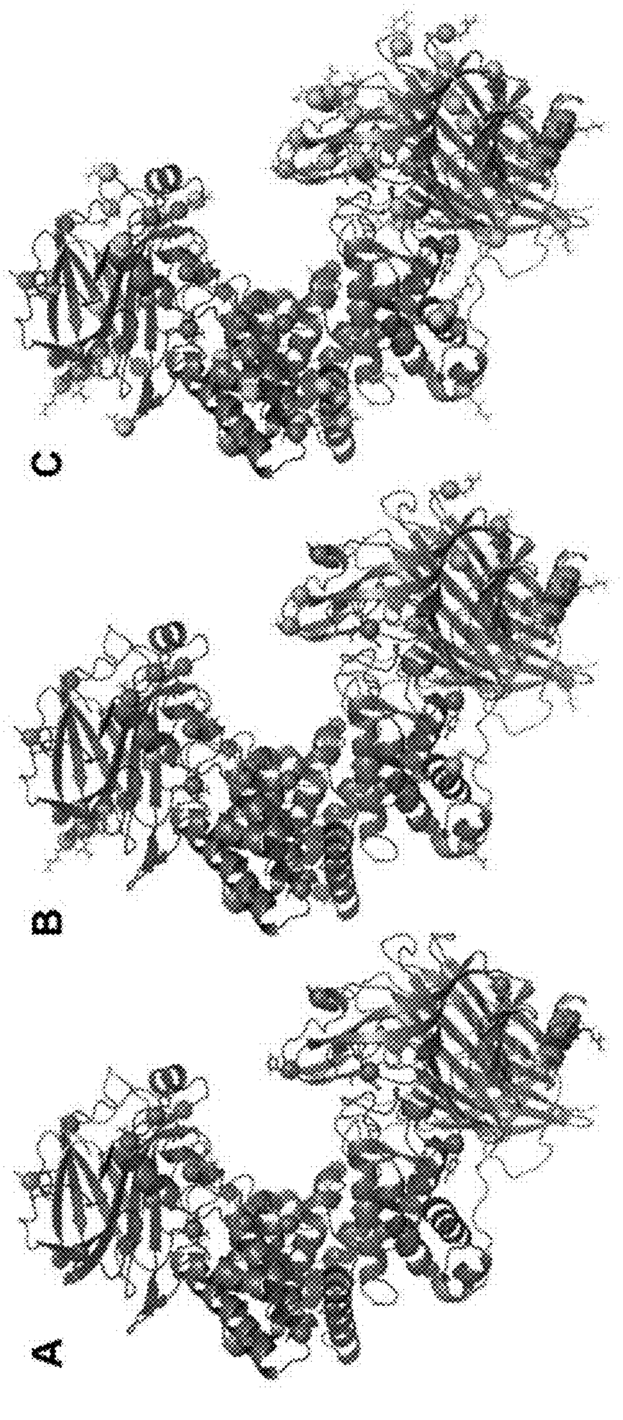

FIG. 3: Computational modeling of designed ChABC mutants. Designed ChABC from *P. vulgaris* using PROSS, with mutated residues for A) ChABC-37-SH3, B) ChABC-55-SH3, and C) ChABC-92-SH3 in red, orange, and yellow balls, highlighting additional mutations between designs.

FIG. 4: Global relaxation of wild type ChABC and designed mutants using Rosetta. A) Wild type ChABC and mutants (ChABC-37, ChABC-55, ChABC-92) were relaxed 2000 times each using the FastRelax Rosetta protocol. The result of each relax run is plotted as the predicted energy vs. the backbone root-mean-square deviation (RMSD) from 1HN0. The lower energy designs are predicted to be more stable. B) Wild type ChABC and mutants (ChABC-37, ChABC-55, ChABC-92) as well as subsets of the ChABC-37 mutations for each domain1-4, having residue ranges 25-242, 243-604, 605-882, 883-1021, and 9, 18, 7, 4 mutations, respectively, were designed with the Rosetta FastDesign™ protocol. The energy of each design relative to the mean wild type energy is plotted overlaid with a boxplot (ggplot2::geom_boxplot default parameters; mid: median, hinge: 25-75% quantile, and whiskers: 1.5 times inter quantile range of the hinge). C) Wildtype ChABC mutations, and prior art mutations designed with the Rosetta FastDesign protocol as in Upper Right panel.

Figure 5:
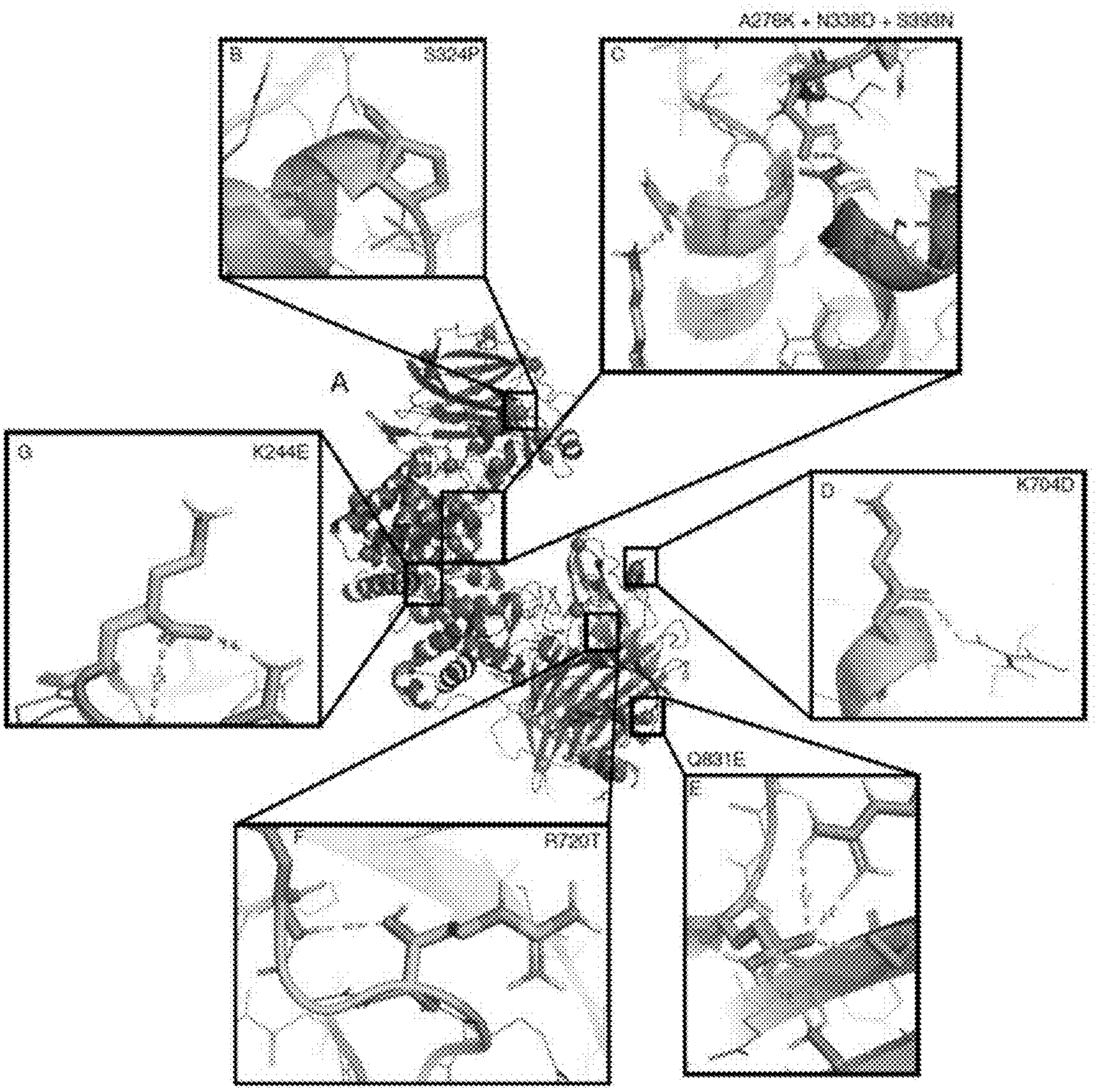

FIG. 5: Example mutations from ChABC-37-SH3. A) 1HN0 colored by domain as FIG. 3 with residues mutated in ChABC-37-SH3 in magenta. In boxes, native residues shown in yellow, mutant residues shown in magenta. B) Introducing proline reduces conformational entropy. C) 3 mutations coordinately stabilize the helix termini. D,E) Introducing charge-charge interactions increases resistance to aggregation. F,G) Introducing polar H-bonds stabilizes loops.

Figure 6:

FIG. 6: Residues mutated in prior work. 1HN0 colored as in FIG. 3 with all 37 residues mutated in prior studies listed in Table 1.

Figure 7:

FIG. 7: ChABC-SH3 Model. ChABC (pdb: 1HN0) modeled with N-terminal SH3 domain (pdb: 1JO8) with different colors representing individual domains.

Figure 8:
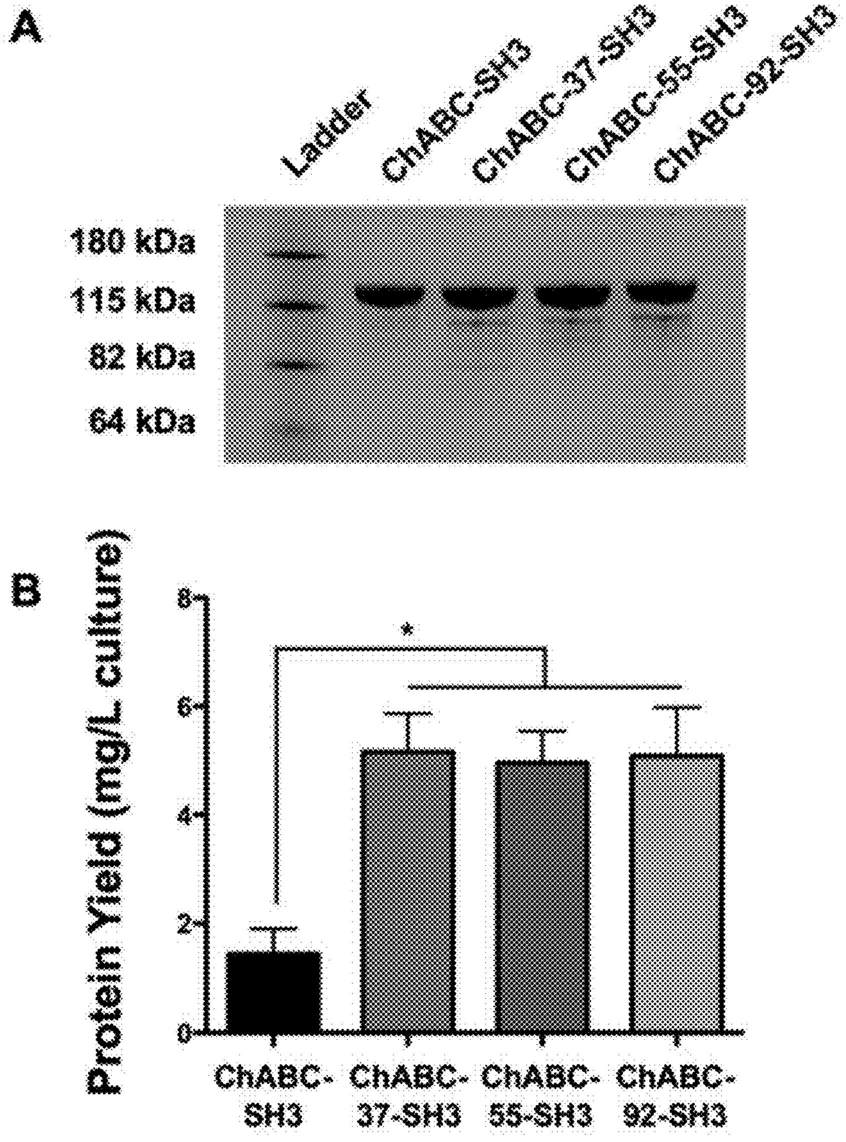

FIG. 8: ChABC-SH3 designs are highly expressed. A) Gel electrophoresis of 5 g of ChABC-SH3 and mutated designs followed by Coomassie Brilliant Blue staining of protein bands. B) ChABC-SH3 and mutant yield from large volume (2 L) *E. coli* cultures (n=3, mean±SD, *p<0.05).

Figure 9:
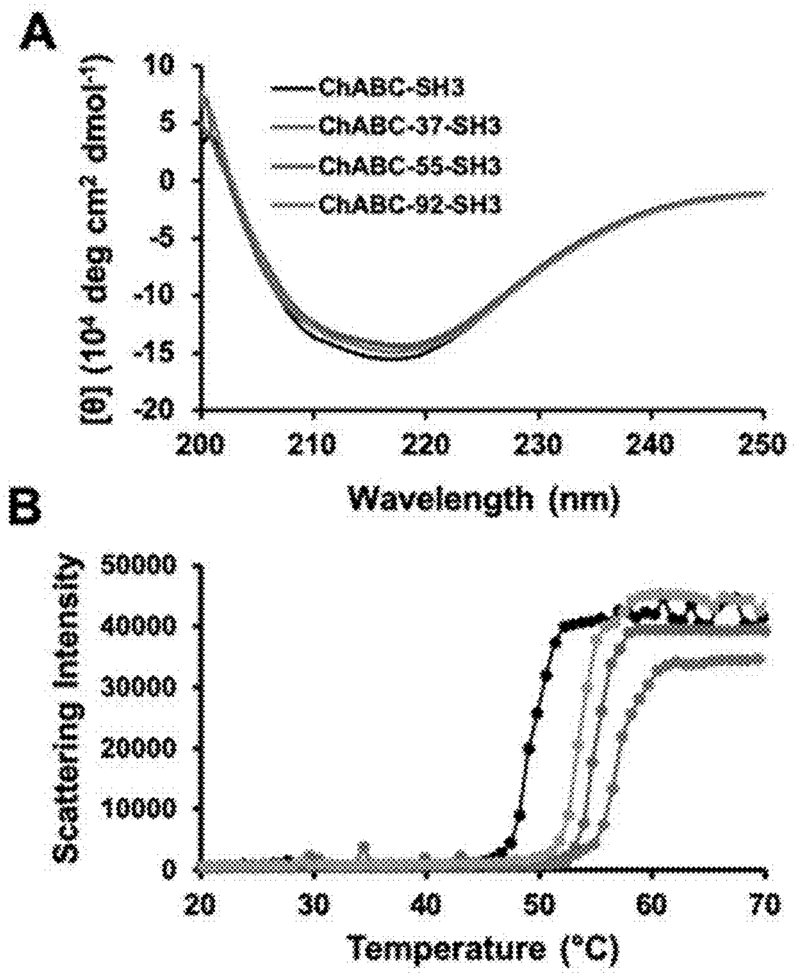

FIG. 9: ChABC-SH3 designs are more stable than wild type. A) Circular dichroism spectra of ChABC-SH3 and designs from 200 to 250 nm at 25° C. B) Protein aggregation curves over 20-70° C. (1° C./min) measured by scattering intensity of solution.

Figure 10:
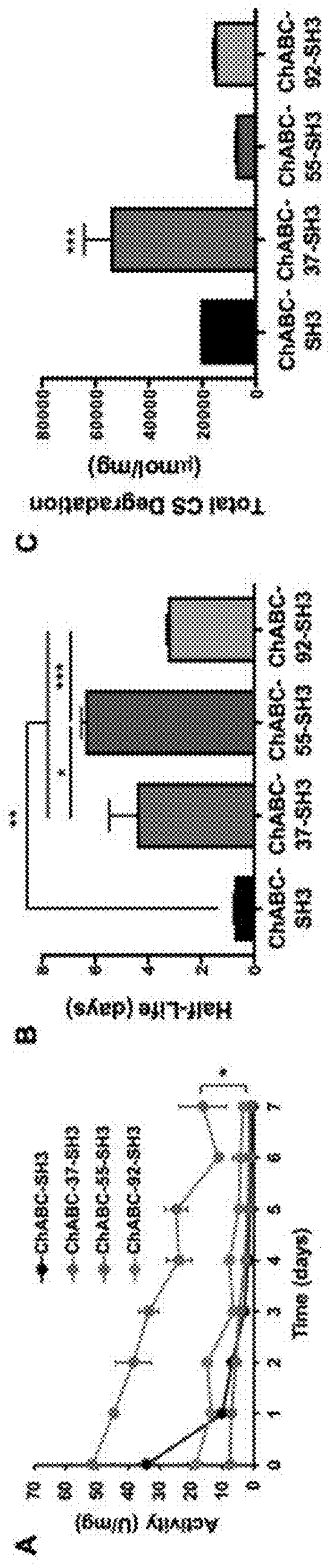

FIG. 10: ChABC-37-SH3 retains activity longer than wild type. A) Specific activity of wild type and mutants after incubation at 37° C. in 0.1% BSA in PBS for 7 d. (*p<0.05 for ChABC-37-SH3 vs. ChABC-SH3 at all time points) B) Half-life of ChABC-SH3 and mutants based on specific activity. (*p<0.05, p<0.01, *p<0.001) C) Total CS degradation as measured by area under the activity curve of ChABC-SH3 and mutants over 7 days. (***p<0.001 compared to all other groups) (n=3, mean±SD)

Figure 11:
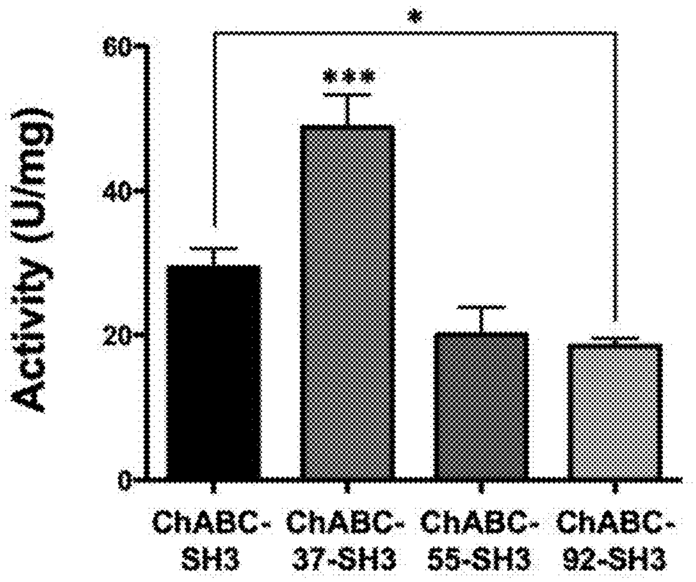

FIG. 11: ChABC-37-SH3 mutant demonstrates higher initial activity for dermatan sulfate compared to ChABC-SH3 and other mutants. (n=3, mean±SD, *p<0.05, ***p<0.001 compared to all other groups)

Figure 12:
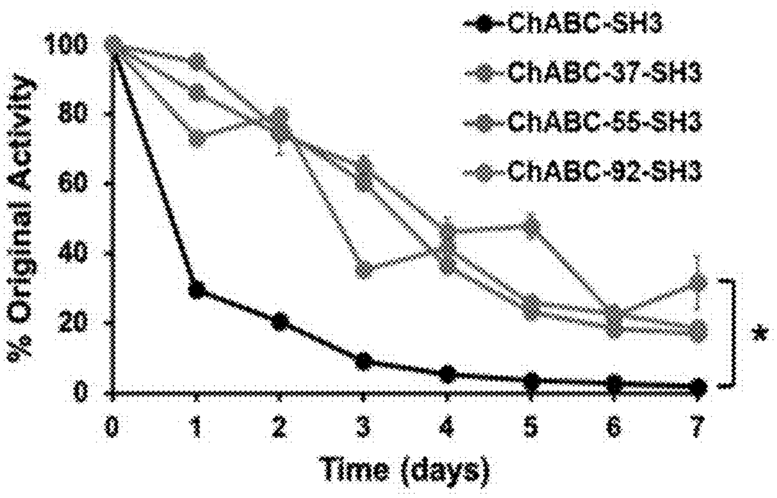

FIG. 12: Activity of wild type ChABC-SH3 and mutants for chondroitin sulfate A plotted as percentage of original activity. ChABC-SH3 and mutants were incubated at 37° C. in 0.1% BSA in PBS for 7 d. (*p<0.05 for ChABC-SH3 vs. ChABC-37-SH3 at all time points) (n=3, mean±SD)

Figure 13:
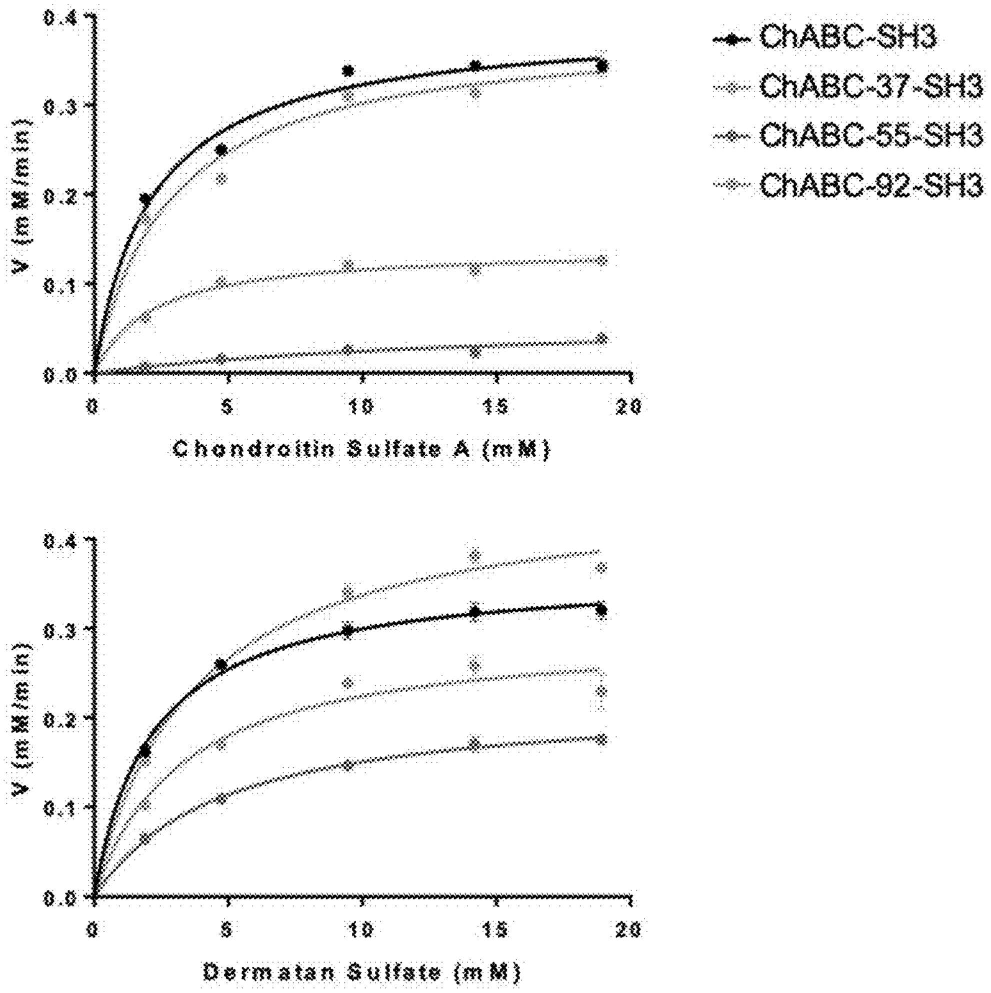

FIG. 13: Michaelis-Menten graphs for the activity of ChABC-SH3 and mutants. Enzymatic activity was measured using two substrates of ChABC: A) chondroitin sulfate A, and B) dermatan sulfate.

Figure 14:
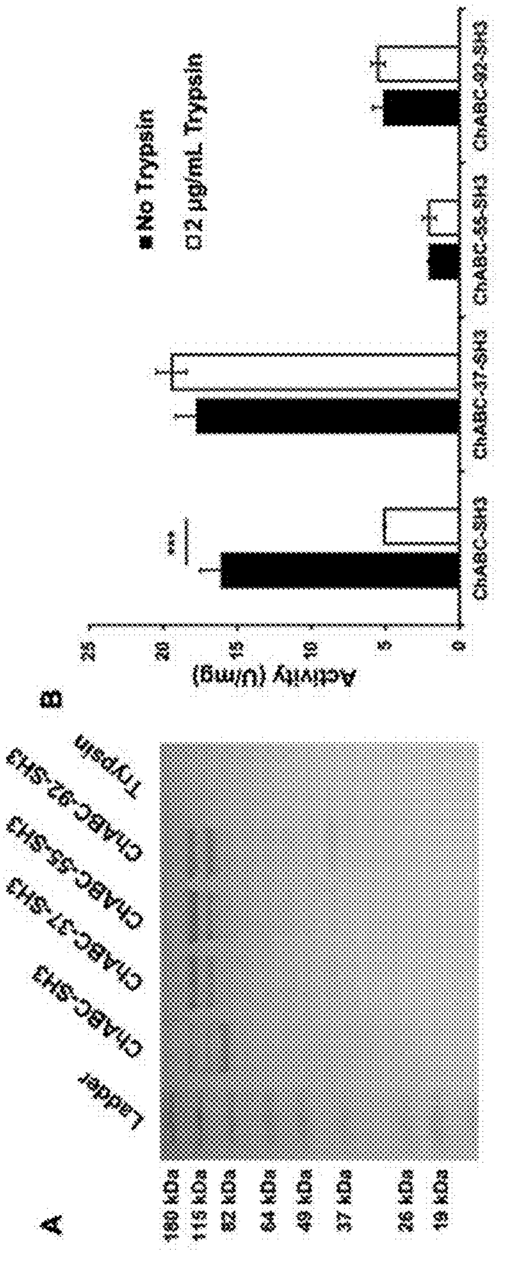

FIG. 14: ChABC-SH3 designs are more resistant to proteolytic degradation than wild type ChABC-SH3. Proteins were incubated in buffer (10 mM $CaCl_2$, 20 mM Tris) with or without 2 g/mL of trypsin for 45 minutes at room temperature. A) Gel electrophoresis and Coomassie Brilliant Blue staining of ChABC-SH3 and mutated designs after trypsin treatment. B) Specific activity of wild type ChABC-SH3 and mutants for chondroitin sulfate A with or without trypsin treatment. (***p<0.001 compared to all other groups) (n=3, mean±SD)

Figure 15:
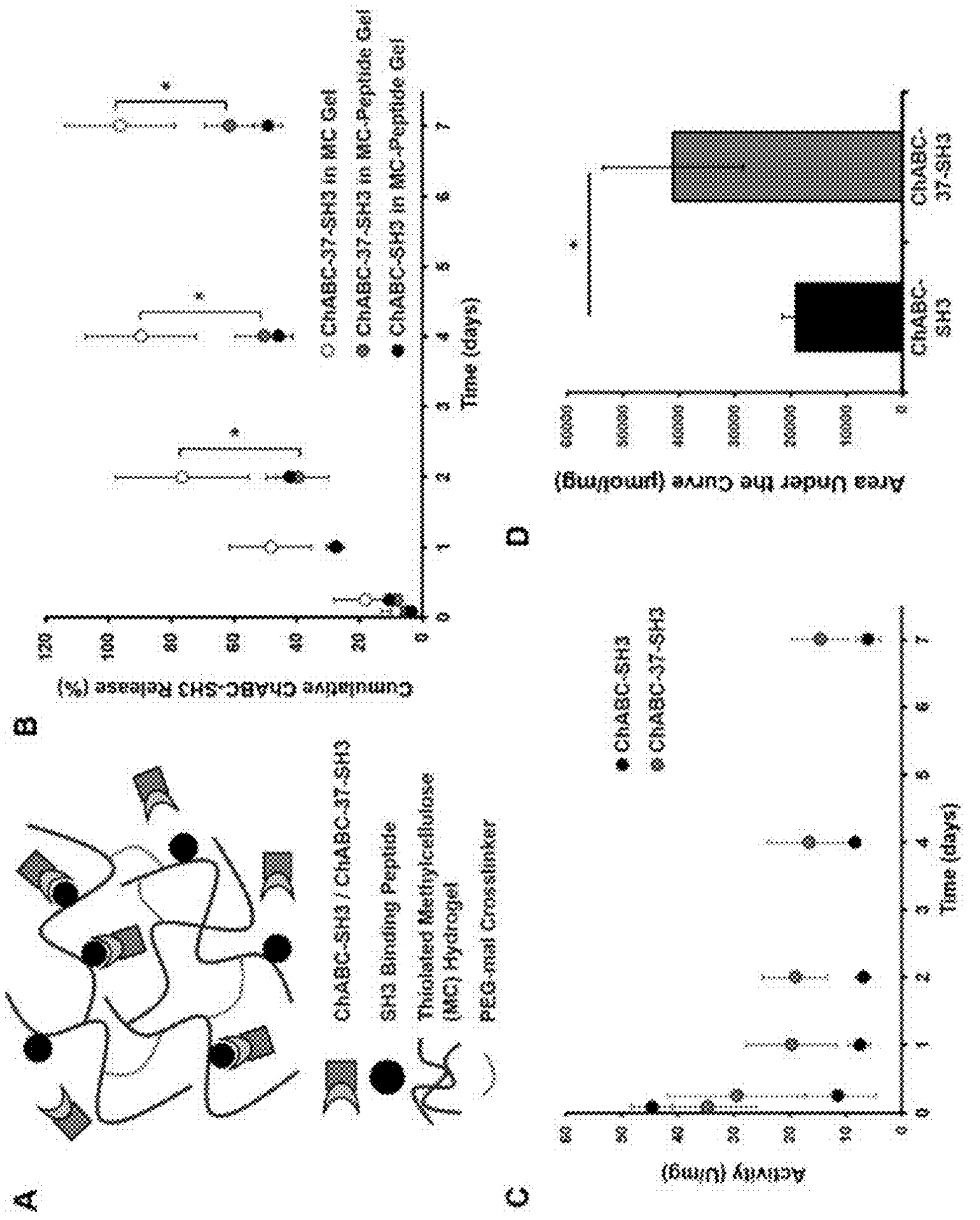

FIG. 15: Release of bioactive ChABC-SH3 and ChABC-37-SH3 is sustained over 7 days from crosslinked methylcellulose (MC) hydrogels covalently modified with SH3 binding peptides. A) Crosslinked MC-peptide hydrogels for affinity-controlled release. B) 20 g of ChABC-SH3 or ChABC-37-SH3 were mixed into 100 μL of MC hydrogel alone or modified with SH3 binding peptides. The hydrogels released protein into aCSF over 7 d. Release was plotted as percentage of total protein loaded. (*p<0.05) C) Specific activity of ChABC-SH3 and ChABC-37-SH3 released from methylcellulose hydrogels over 7 d. D) Area under the activity curve of ChABC-SH3 and ChABC-37-SH3 mutant over 7 d release from hydrogels. (*p<0.05) (n=3, mean±SD)

Figure 16:
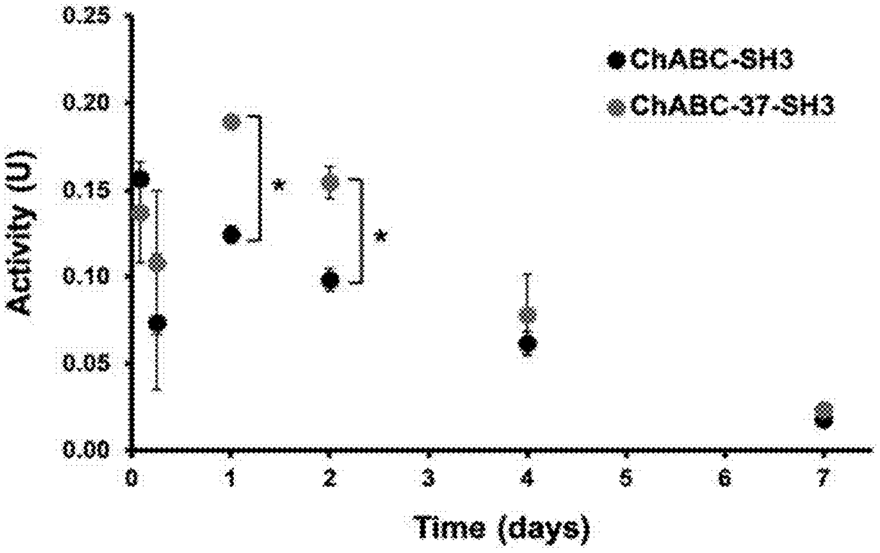

FIG. 16: Activity of ChABC-SH3 and ChABC-37-SH3 released from methylcellulose hydrogels containing affinity binding peptides. 20 g of ChABC-SH3 or ChABC-37-SH3 were mixed into 100 μL of methylcellulose hydrogel modified with SH3 binding peptides. The hydrogels released protein into artificial cerebrospinal fluid over 7 d, and the enzymatic activity of the protein was evaluated using chondroitin sulfate A as the substrate. (*p<0.05) (n=3, mean±SD)

Figure 17:
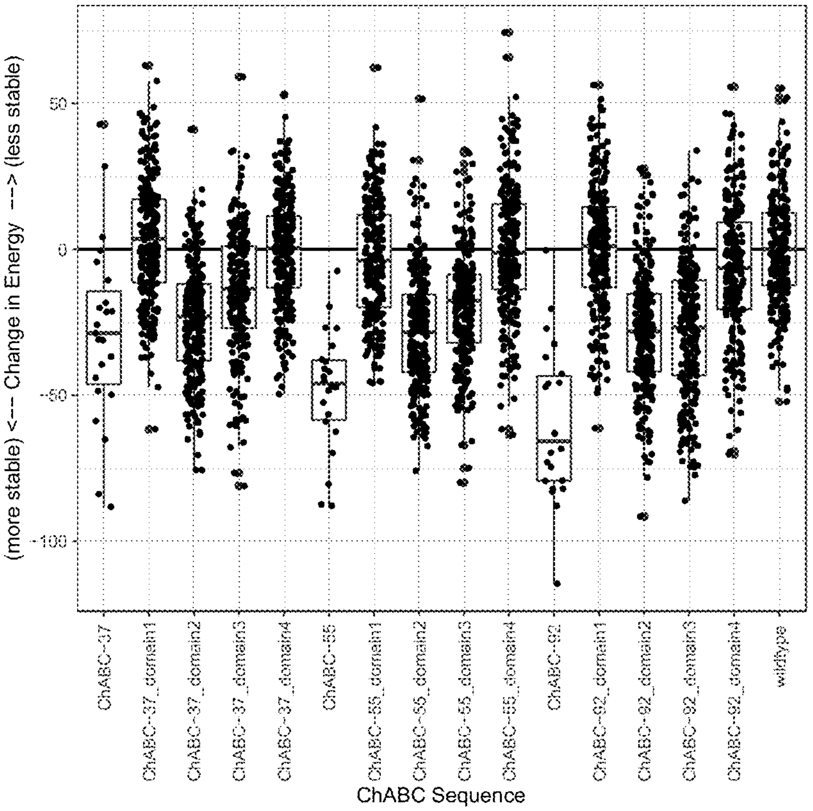

FIG. 17: Improved stability contribution from mutations in Domains 2 and 3. Wild type ChABC and mutants (ChABC-37, ChABC-55, ChABC-92) as well as subsets of the ChABC-37, ChABC-55, ChABC-92 mutations for each domain1-4, having residue ranges 25-242, 243-604, 605-882, 883-1021, were designed with the Rosetta FastDesign™ protocol. The energy of each design relative to the mean wild type energy is plotted overlaid with a boxplot (ggplot2::geom_boxplot default parameters; mid: median, hinge: 25-75% quantile, and whiskers: 1.5 times inter quantile range of the hinge).

DETAILED DESCRIPTION

Definitions

Unless defined otherwise, all technical and scientific terms used herein have the same meaning as commonly understood by one of ordinary skill in the art to which this invention belongs.

The term "about" as used herein refers to the usual error range for the respective value readily known to the skilled person in this technical field.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "functional half-life" as used herein in relation to enzyme activity, refers to the time for the activity of an enzyme to drop by half, when measured under physiological conditions.

A "fusion" protein is a protein wherein a first polypeptide is operably linked, e.g., directly or indirectly, to a second polypeptide.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention. Host cells may be prokaryotic cells or eukaryotic cells.

The term "pharmaceutical composition" as used herein refers to a preparation that is in such form as to permit the biological activity of the active ingredient to be effective, and that contains no additional components that are unacceptably toxic to a subject to which the formulation would be administered. Such formulations are sterile.

The term "subject" refers to any healthy animal, mammal or human, or any animal, mammal or human afflicted with a disease or disorder. The term "subject" is interchangeable with "patient."

The term "vector" as used herein refers to a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "wild-type" and "wild-type sequence" as used herein refer to protein or a sequence of amino or nucleic acids that occurs naturally within a certain population (e.g., human, mouse, rats, cell, etc.).

The present application relates to mutants of Chondroitinase ABC lyase I (ChABC) that demonstrate improved stability over the wild-type enzyme, and over previously known mutants of ChABC.

ChABC is an enzyme that depolymerizes glycosaminoglycans with broad specificity. It can promote tissue and functional recovery following central nervous system injury by degrading inhibitory proteoglycans in the glial scar. However, as described above, the use of ChABC for in vivo therapeutic applications is limited due to its extremely short functional half-life (~16 hours) at physiological temperatures (37° C.) and difficulty achieving sustained, local presentation within the injury site. This enzyme is very fragile and needs to be delivered directly to the tissue in order to be effective; hence both the stability of the enzyme and its delivery have significantly limited its commercialization.

ChABC comprises for domains, with domain 2 containing the catalytic site.[3] With reference to the sequence of ChABC from *Proteus vulgaris* (Uniprot entry: CABC1_PROVU; SEQ ID NO:1), the enzyme comprises 1021 amino acid residues, with four adjacent domains: Domain 1 is amino terminal domain extending from residue 38 to residue 231; Domain 2 comprises the catalytic site and extends from residue 243 to residue 604; and Domain 3 is a super-sandwich domain extending from residue 623 to residue 882, as identified by Pfam 31.0.3 Domain 4 is the C-terminal domain that extends from residue 901 to residue 967.3 Reference herein to sequence position numbers is based on the sequence numbering of SEQ ID NO:1, although homologues of the ChABC from *P. vulgaris* have the same or similar domains.

The present application provides ChABC mutant variants having a functional half-life that is at least 4 times or 4.5 times longer than that of the corresponding wild-type enzyme. In some embodiments, the half-life is at least 6 times longer than that of the wild-type enzyme. This demonstrates a significantly improved stability over that of wild-type ChABC.

The term "wild-type ChABC" is used herein to reference any naturally occurring ChABC. Although the following discussion and Examples specifically reference ChABC from *P. vulgaris*, the skilled person would recognize that there are ChABC homologues from other species. Such homologues are readily identified, for example, by reference to ChABC enzyme identified in Uniprot, by considering phylogenetic/sequence similarity (e.g., using a BlastP E-value<$1e^{50}$) and/or functional similarity (e.g., those with annotated Chondroitin sulfate ABC endolyase (EC: 4.2.2.20), and/or chondroitin-sulfate-ABC exolyase (EC: 4.2.2.21) activity.

Point mutations in domains 2 and 3 of wild-type ChABC have now been found to contribute to improved stability in the ChABC mutants of the present application. In some embodiments the present application provides ChABC mutants comprising at least 15 point mutations, or at least 18 point mutations, in domain 2 of the wild-type enzyme and/or at least 5 point mutations, or at least 7 point mutations, in domain 3 of the wild-type enzyme. In some embodiments, the ChABC mutant comprises from 15 to 40 point mutations, or from 18 to 35 in domain 2 of the wild-type enzyme. In other embodiments, the ChABC mutant comprises from 5 to 30 mutations in domain 3 of the wild-type enzyme. In yet further embodiments, the ChABC mutant comprises from 15 to 35 point mutations in domain 2 of the wild-type enzyme and from 5 to 35 point mutations, or from 7 to 30 point mutations, in domain 3 of the wild-type enzyme.

In certain embodiments, the ChABC mutants include the specific point mutations listed below with reference to SEQ ID NO:1. In other embodiments, the ChABC mutants are mutants of a wild-type ChABC that is homologous to the ChABC having the amino acid of SEQ ID NO:1. Homologues of a polypeptide will possess high degree of sequence or structural similarity when aligned using standard methods. The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn, and tblastx. A description of how to determine sequence identity and sequence homology using this program is available on the NCBI website. As used herein, the term "homologous" is used in reference to homologous ChABCs to reference ChABCs with amino acid sequences that when aligned with the amino acid of SEQ ID NO:1 have a BLAST expectation value (BLAST E-value) of less than $1e^{-50}$.

In particular embodiments, there is provided a mutant ChABC comprising: at least 18 point mutations in domain 2 of the amino acid sequence of SEQ ID NO:1 or an amino acid sequence that is homologous to the amino acid sequence of SEQ ID NO:1, wherein the at least 18 point mutations in domain 2 are selected from K244E, Q246L, L247P, V249A, 1257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, V470L, N471H, S517A, S529E, N536Q, K583P, S592A, A596R, and D599G based on the amino acid sequence of SEQ ID NO:1, or selected from corresponding point mutations in the homologous amino acid sequence.

In one example, the ChABC mutant comprises the following 18 mutations K244E, 1257V, A278K, L308I, I314K, N321H, S324P, N338D, S347A, E353N, S393N, T401A, A438P, K465E, V470L, N471H, S517A, and K583P, based on SEQ ID NO:1, or corresponding point mutations in the homologous amino acid sequence. In another example, there is provided a ChABC mutant comprising the following 23 mutations K244E, Q246L, V249A, 1257V, A278K, L308I, I314K, N321H, S324P, N338D, S347A, E353N, S393N, T401A, S437G, A438P, K465E, V470L, N471H, S517A, N536Q, K583P, and A596R, based on SEQ ID NO:1, or corresponding point mutations in the homologous amino acid sequence. In a further example, there is provided a ChABC mutant comprising the following 34 mutations K244E, Q246L, L247P, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, N471H, S517A, S529E, N536Q, K583P, S592A, A596R, and D599G, based on SEQ ID NO:1, or corresponding point mutations in the homologous amino acid sequence.

In particular embodiments, there is provided a ChABC mutant comprising at least 7 point mutations in domain 3 of the amino acid sequence of SEQ ID NO:1 or an amino acid sequence that is homologous to the amino acid sequence of SEQ ID NO:1, wherein the at least 7 point mutations in domain 3 are selected from Q636G, A644G, T647K, N656T, N656H, V669T, N675Y, L679K, Q685E, Q686N, E694P, K704D, K704E, D705E, K710N, R720T, 1740Q, A743Q, E746P, K779Y, E805T, N806Q, N806T, Q814T, Q814G, Q831E, V843T, E846D, T866R and D870N, or selected from corresponding point mutations in the homologous amino acid sequence.

In one example, there is provided a ChABC mutant comprising the following 7 mutations N656H, N675Y, Q685E, E694P, K704D, R720T, and Q831E, based on SEQ ID NO:1, or corresponding point mutations in the homologous amino acid sequence. In another example, there is provided a ChABC mutant comprising the following 12 mutations A644G, N656T, N675Y, Q685E, E694P, K704D, K710N, R720T, N806T, Q814T, Q831E, and T866R, based on SEQ ID NO:1, or corresponding point mutations in the homologous amino acid sequence. In another example, there is provided a ChABC mutant comprising the following 26 mutations Q636G, A644G, T647K, N656T, V669T, N675Y, L679K, Q685E, Q686N, E694P, K704E, D705E, K710N, R720T, 1740Q, A743Q, E746P, K779Y, E805T, N806Q, Q814G, Q831E, V843T, E846D, T866R and D870N, based on SEQ ID NO:1, or corresponding point mutations in the homologous amino acid sequence.

In some embodiments, the ChABC mutant comprises at least 37 point mutations from the wild-type enzyme and includes point mutations in both domain 2 and domain 3.

The ChABC mutants provide herein optionally comprise additional comprise mutations in regions other than domains 2 and 3 of the wild-type enzyme.

The present inventors have designed a series of ChABC mutants, using the algorithm Protein Repair One Stop Shop. Exemplary mutants were prepared and studied as described in the following Examples. The three mutants studied in the Examples had 37 (the "37 mutant ChABC"), 55 (the "55 mutant ChABC) or 92 (the "92 mutant ChABC") mutations and were manufactured as described and comprise amino acid sequences of SEQ ID NOs: 2, 3 and 4, respectively. These ChABC mutants were tested for stability and bioactivity. The 37 mutant ChABC was found to be significantly more stable, and was highly bioactive for 7 days; relative to wild-type ChABC, this mutant ChABC has 6.5 times greater functional half-life, 6° C. increase in melting temperature (indicative of structural stability), and a 5-fold increase in protein expression in *E. coli.*

As illustrated in FIG. 17, point mutations in Domains 2 and 3 of ChABC contributed significantly to the improved stability of the mutant ChABC.

The ChABC mutants of the present application exhibit improved stability over other ChABC mutants that have been made, each of which comprise no more than three point mutations. Interestingly, the mutants described herein retained ChABC activity and provided a much greater improvement in stability over mutants having only single point mutations in domain 2 or domain 3, as determined from a comparison of the amount by which the half-life of the respective mutants varied from that of the wild-type enzyme. The comparisons are summarized in Table 1.

TABLE 1

Summary of ChABC stabilization studies. Each row represents a mutant or construct with columns for the study source, ChABC Gene, construct and buffer, sequence mutation from wild type, substrate, and measured activities where available, including specific activity, $V_{max}$, $K_m$, $k_{cat}$, $k_{cat}/K_m$, $T_m$, and $t_{1/2}$ in normalized units.

| Modifications | $V_{max}$ (μM/min) | $K_m$ (μM) | $k_{cat}$ ($min^{-1}$) | $k_{cat}/K_m$ ($μM^{-1}\ min^{-1}$) | $T_m$ (° C.) | $ΔT_m$ (° C.) | Half-Life @ 37° C. (min) | Study |
|---|---|---|---|---|---|---|---|---|
| ChABC-SH3 | 392 | 2132, 2175 | 4894, 4560 | 2.30, 210 | 49 | — | 991 | Current Invention[2] |
| ChABC-37-SH3 | 387 | 2821, 3655 | 4640, 5759 | 1.72, 1.58 | 55 | 6 | 6299 | |
| ChABC-55-SH3 | 64 | 16180, 4778 | 802, 2776 | 0.05, 0.58 | 57 | 8 | 9104 | |
| ChABC-92-SH3 | 140 | 2120, 3297 | 1753, 3722 | 0.83, 1.14 | 53 | 4 | 4626 | |
| Wild type | 0.028 | 44 | 5090 | 116 | 47 | — | 2 | (Nazari-Robati, et al. 2012)[1] |
| With glycerol | 0.026 | 39 | 4727 | 121 | 49 | 2 | 30 | |
| With sorbitol | 0.023 | 33 | 4182 | 127 | 52 | 5 | 50 | |
| With trehalose | 0.025 | 35 | 4545 | 130 | 54 | 7 | 80 | |
| Wild type | | 42 | 4980 | 120 | 47 | — | 2 | (Nazari-Robati, et al. 2013)[1] |
| Q140G | | 34 | 5340 | 156 | 50 | 3 | 5 | |
| Q140A | | 31 | 5280 | 168 | 53 | 6 | 7 | |
| Q140N | | 50 | 4800 | 96 | 45 | −2 | 1.5 | |
| Wild type | 18.7, 5.04 | 73.1, 8.17 | 35088, 9396 | 480, 1150 | | | | (Chen, et al. 2015)[1,2] |
| D433A | | | | | | | | |
| S441A | | | | | | | | |
| N468A | | | | | | | | |
| S474A | | | | | | | | |
| N515A | | | | | | | | |
| N564A | | | | | | | | |
| Y575A | | | | | | | | |
| Y594A | | | | | | | | |
| F609A | | | | | | | | |
| Y623A | | | | | | | | |
| R660A | | | | | | | | |
| N795A | 22.5, 4.59 | 7.25, 13.65 | 21859, 10008 | 3015, 733.2 | | | | |
| W818A | 19.84, 2.94 | 16.92, 2.29 | 15055, 8029 | 890, 3506 | | | | |
| Wild type | 0.029 | 40.2 | 5140 | 128 | 47 | — | 3.8 | (Shirdel, et al. 2015)[1] |
| R692L | 0.045 | 47.3 | 7000 | 148 | 43 | −4 | 3.5 | |
| H700A | 0.039 | 49.2 | 6877 | 140 | 45 | −2 | 3.5 | |
| H700N | 0.045 | 42.2 | 12,971 | 307 | 41 | −6 | 10 | |
| L701T | 0.028 | 56.7 | 4763 | 84 | 57 | 10 | 7.5 | |
| Q787A | 0.028 | 40.3 | 5000 | 124 | 51 | 4 | 2.5 | |
| H700N, L701T | 0.024 | 48.8 | 3703 | 76 | 63 | 16 | 15.8 | |
| R692L, H700A | 0.05 | 27.6 | 13,210 | 479 | 39 | −8 | 2.3 | |
| R692L, Q787A | 0.095 | 28.3 | 14,875 | 526 | 37 | −10 | 2.2 | |
| H700A, Q787A | 0.106 | 29.9 | 16,562 | 554 | 35 | −12 | 1.9 | |
| R692L, H700A, Q787A | 0.116 | 34.3 | 23,200 | 676 | 33 | −14 | 1.5 | |

TABLE 1-continued

Summary of ChABC stabilization studies. Each row represents a mutant or construct with columns for the study source, ChABC Gene, construct and buffer, sequence mutation from wild type, substrate, and measured activities where available, including specific activity, $V_{max}$, $K_m$, $k_{cat}$, $k_{cat}/K_m$, $T_m$, and $t_{1/2}$ in normalized units.

| Modifications | $V_{max}$ (μM/min) | $K_m$ (μM) | $k_{cat}$ ($min^{-1}$) | $k_{cat}/K_m$ ($μM^{-1}$ $min^{-1}$) | $T_m$ (° C.) | $ΔT_m$ (° C.) | Half-Life @ 37° C. (min) | Study |
|---|---|---|---|---|---|---|---|---|
| Wild type | 0.03 | 41.6 | 5317 | 128 | | | 3.9 | (Shamsi, et al. 2016)[1] |
| L679S | 0.044 | 40.6 | 10682 | 263 | | | 6.6 | |
| L679D | 0.029 | 41.8 | 5178 | 124 | | | 9.5 | |
| Wild type | 0.012 | 0.52 | 2223 | 4254 | 48 | — | 8.3 | (Kheirollahi, et al. 2017)[1] |
| E131P | 0.014 | 0.692 | 2072 | 3427 | 48 | 0 | 9.6 | |
| K132P | 0.013 | 0.84 | 2028 | 2414 | 48 | 0 | 5.4 | |
| I134P | 0.015 | 0.75 | 2438 | 3223 | 48 | 0 | 4.4 | |
| T136P | 0.012 | 0.48 | 2034 | 4172 | 48 | 0 | 6.4 | |
| E138P | 0.015 | 0.76 | 2238 | 2920 | 50 | 2 | 18 | |
| Wild type | 0.0295 | 40.8 | 5090 | 125 | | | 3.8 | (Moradi, et al. 2017)[1] |
| M889K | 0.0502 | 27.7 | 13319 | 481 | | | 9.1 | |
| M889L | 0.0296 | 43.4 | 5045 | 116 | | | 2.9 | |
| L679D, M889K | 0.1055 | 30 | 16484 | 549 | | | 11.4 | |
| L679S, M889K | 0.0436 | 41 | 12262 | 299 | | | 6 | |
| Wild type | | 0.6624 | 3433.6 | 5183.74 | | | | (Shahaboddin, etal. 2017)[1] |
| N806Y, Q810Y | | 0.398 | 2571.8 | 6461.83 | | | | |
| N806A, Q810A | | 0.6099 | 4395 | 7206.09 | | | | |
| N806A, Q810Y | | 0.9494 | 1860.6 | 1959.76 | | | | |
| N806Y, Q810A | | 1.037 | 2838.6 | 2737.34 | | | | |
| Wild type | 0.01073 | 662.4 | 3433.6 | 5.18374 | | | | (Shahaboddin, et al. 2018)[1] |
| I295Y | Inactive | — | — | — | | | | |
| S581Y | 0.01022 | 614.8 | 3289.3 | 5.35024 | | | | |
| G730Y | 0.009087 | 388.1 | 2368.7 | 6.10307 | | | | |
| Wild type | 0.007321 | 0.66 | 3669 | 5542.2 | | | 22.2 | (Maleki, et al. 2018)[1] |
| S474H | 0.008461 | 0.77 | 4231 | 5436.2 | | | 10.6 | |
| H475A | Inactive | — | — | — | | | — | |
| Y476H | Inactive | — | — | — | | | — | |
| Y476A | Inactive | — | — | — | | | — | |
| H475A, Y476H | Inactive | — | — | — | | | — | |
| Wild type | 0.01 | 0.57 | 2426 | 4257 | 48 | — | 8.5 | (Kheirollahi, et al. 2018)[1] |
| E138A | 0.0136 | 0.82 | 2321 | 2831 | 48 | 0 | 9.9 | |
| E138K | 0.015 | 1.06 | 1211 | 1143 | 48 | 0 | 9.9 | |
| E138D | Inactive | — | — | — | 42 | −6 | — | |
| E138P, Q140A | 0.011 | 0.57 | 4421 | 7756 | 49 | 1 | 1.3 | |
| E138P | 0.015 | 0.76 | 2238 | 2920 | 50 | 2 | 18 | |
| Wild type | | | | | 48 | — | 606 | (Hettiaratchi, et al. 2019)[1] |
| N1000G | | | | | 49 | 1 | 1218 | |
| Q140G | | | | | 49 | 1 | 444 | |
| T154F | | | | | 49 | 1 | 84 | |
| S431L | | | | | 50 | 2 | 198 | |
| Wild type | 0.028 | 40.4 | 5224 | 129 | 48 | — | | (Mohammadyari, et al. 2019)[1] |
| Q678E | 0.03 | 42.5 | 5093 | 120 | 47 | −1 | | |
| Q681E | 0.04 | 51 | 7005 | 137 | 49 | 1 | | |
| Q678E, Q681E | 0.046 | 48.5 | 7165 | 148 | 51 | 3 | | |

Parameters determined using [1]chondroitin sulfate A or [2] dermatan sulfate as the substrate.

Each of the ChABC mutants provided herein retain at least 70% activity, at least 75% activity, at least 80% activity, or at least 85% activity, after 2 days at 37° C. and a pH of approximately 7.4.

Protein Variants and Modifications

Proteins that vary from the present mutant ChABCs (e.g., SEQ ID NO:2, 3 or 4) as a result of one or more conservative amino acid substitutions are provided herein. In particular, conservative variants of the mutant ChABC (e.g., SEQ ID NO:2, 3 or 4) comprise one or more substitution of an amino acids for an amino acid residue having a similar biochemical property (such as 1-4, 1-8, 1-10, 1-20, 5-50, 10-25, or 5-10 conservative substitutions). Typically, conservative substitutions have little to no impact on the activity of a resulting peptide. For example, a conservative substitution is an amino acid substitution in the amino acid sequence of a mutant ChABC that does not substantially affect the ability of the mutant to degrade a polysaccharide, such as a glycosaminoglycan (including, for example, chondroitin sulfate, dermatan sulfate and heparin sulfate). Examples of amino acids which may be substituted for an original amino acid in a protein and which are regarded as conservative substitutions include: Ser for Ala; Lys, Gln, or Asn for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met;

Met, Leu or Tyr for Phe; Thr for Ser; Ser for Thr; Tyr for Trp; Trp or Phe for Tyr; and Ile or Leu for Val.

A mutant ChABC (e.g., SEQ ID NO:2, 3 or 4) can be modified, e.g., to improve stability or its pharmacological profile. Exemplary chemical modifications include, e.g., adding chemical moieties, creating new bonds, and removing chemical moieties. Modifications at amino acid side groups include acylation of lysine F-amino groups, N-alkylation of arginine, histidine, or lysine, alkylation of glutamic or aspartic carboxylic acid groups, and deamidation of glutamine or asparagine. Modifications of the terminal amino group can include des-amino, N-lower alkyl, N-di-lower alkyl, and N-acyl modifications. Modifications of the terminal carboxyl group can include amide, lower alkyl amide, dialkyl amide, and lower alkyl ester modifications.

In some embodiments, the mutant ChABC (e.g., SEQ ID NO:2, 3 or 4) is modified to include a water-soluble polymer, such as polyethylene glycol (PEG), PEG derivatives, polyalkylene glycol (PAG), polysialyic acid, or hydroxyethyl starch.

In some examples, the mutant ChABC (e.g., SEQ ID NO:2, 3 or 4) is PEGylated at one or more positions (for example see methods of Niu et al., *J. Chromatog.* 1327:66-72, 2014, herein incorporated by reference).

In some examples, the mutant ChABC (e.g., SEQ ID NO:2, 3 or 4) includes an immunoglobin Fc domain (for example see Czajkowsky et al., *EMBO Mol. Med.* 4:1015-28, 2012, herein incorporated by reference). The conserved Fc fragment of an antibody can be incorporated either N-terminal or C-terminal of the protein, and can enhance stability of the protein and therefore serum half-life. The Fc domain can also be used as a means to purify the proteins on Protein A or Protein G sepharose beads.

In other examples, the mutant ChABC (e.g., SEQ ID NO:2, 3 or 4) can be incorporated in a fusion protein. Such fusion proteins can be made using techniques known to those skilled in the art, for example, to facilitate targeting, delivery and/or release of the ChABC mutant, to further improve the stability of the ChABC mutant, to facilitate targeting of the ChABC mutant, or to improve bioavailability or solubility. It should be appreciated that this list is not limiting.

In a specific embodiment the mutant ChABC (e.g., SEQ ID NO:2, 3 or 4) described herein can form part of a fusion protein with the Src Homology 3 (SH3) domain (a mutant ChABC-SH3 fusion protein), which enables controlled release of the mutant ChABC from a hydrogel containing SH3 binding peptides. In combination with the SH3 binding peptide strategy, this present mutant ChABC can improve ChABC-based therapeutic strategies by overcoming the limitations of the thermal instability of the native enzyme. U.S. Pat. No. 9,498,539, which is incorporated herein by reference in its entirety, describes an affinity-based approach for extended release of a bioactive molecule that exploits the specific binding of SH3-domain with short proline-rich peptides. Specifically, a polymer modified with SH3-binding peptides with either a weak affinity or strong affinity for SH3 is used to reversibly bind the fusion protein comprising the SH3-domain. Controlled release of the mutant ChABC-SH3 fusion protein can be achieved by taking advantage of this affinity-based approach.

Production of ChABC Mutants

The ChABC mutants provided herein can be prepared by methods known to those skilled in the art, such as recombinant protein production methods.

In one embodiment, provided herein are polynucleotides encoding the above-described ChABC mutants (e.g., SEQ ID NO: 2, 3 or 4), including fusion proteins comprising the ChABC mutants. Such polynucleotides may further comprise, in addition to sequences encoding the ChABC mutants of the invention, one or more expression control elements. For example, the polynucleotide, may comprise one or more promoters or transcriptional enhancers, ribosomal binding sites, transcription termination signals, or polyadenylation signals, as expression control elements operably linked to the coding sequence for the ChABC mutant.

In certain embodiments, the polynucleotide comprises a nucleic acid sequence that expresses a ChABC mutant as described herein and that has been codon optimized for expression in a host cell. For example, the polynucleotide may be codon optimized for *E. coli* gene expression.

In some examples, the polynucleotide comprises modifications of N-glycosylation sites to improve expression of the mutant ChABC (e.g., based on a bacterial sequence) from mammalian cells.

In another embodiment, provided herein are expression vectors comprising the polynucleotide encoding the mutant ChABC. In another embodiment, provided herein are host cells transformed with the expression vector comprising the polynucleotide encoding the ChABC mutants. Such expression vectors are useful for expression and production of the mutant ChABC from bacterial or eukaryotic host cells.

In a further embodiment, provided herein are methods for producing a mutant ChABC, said method comprising expressing the mutant ChABC in the transformed host cell, wherein the host cell is transformed with the expression vector comprising the nucleic acid encoding a mutant ChABC.

In a further embodiment, the polynucleotide encoding a mutant ChABC (optionally in a vector and/or host cell) comprises a sequence for targeting expression of the mutant ChABC at a target site, or encoding a peptide that will target the mutant ChABC to a target site (e.g., from amyloid precursor protein (Day P., et al., 2020*; PLoS One* 15(1): e0221851)).

Compositions and Uses of the Mutant ChABC

The present application provides compositions that comprise a mutant ChABC (including modifications and variants thereof) as described herein, or a polynucleotide, vector or host cell expressing the mutant ChABC, and carrier or excipient. In particular embodiments, the composition is a pharmaceutical composition comprising a pharmaceutically or physiologically acceptable carrier or excipient.

Such compositions can optionally comprise a suitable amount of a pharmaceutically acceptable excipient so as to provide the form for proper administration. Suitable pharmaceutical excipients can be liquids, such as water, buffers and oils, including those of petroleum, animal, vegetable, or synthetic origin, such as peanut oil, soybean oil, mineral oil, sesame oil and the like. The pharmaceutical excipients can be, for example, saline or buffered saline. In addition, auxiliary, stabilizing, thickening, lubricating, and coloring agents can be used. In one embodiment, the pharmaceutically acceptable excipients are sterile when administered to a subject. Water is a useful excipient when any mutant ChABC described herein is administered intravenously. Saline solutions, in particular buffered saline solutions (e.g., phosphate buffered saline). Suitable pharmaceutical excipients may also include sugars (e.g., trehalose), glycerol, propylene glycol, water, ethanol and the like.

In certain embodiments, the mutant ChABC is formulated as a pharmaceutically acceptable salt. In particular, the mutant ChABC may can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such pharmaceutically acceptable salts are well known in the art.

Optionally, the compositions comprising the mutant ChABC further comprise an enzyme stabilizer, such as a sugar stabilizer (e.g., trehalose), glycerol, another protein, or the like.

Optionally, the composition further comprises an additional therapeutic agent, or the mutant ChABC, or polynucleotide, vector or host cell expressing the mutant ChABC, is formulated for administration with an additional therapeutic agent, by simultaneous administration or by administration before or after the additional therapeutic agent.

The mutant ChABC (alone or in combination with one or more other therapeutic agent) may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed, for example, in Remington: The Science and Practice of Pharmacy, 20th Ed., Alfonso Gennaro, Ed., Philadelphia College of Pharmacy and Science (0.2000).

The compositions, mutant ChABC, and polynucleotide, vector or host cell expressing the mutant ChABC provided herein can be used for a variety of purposes. In some embodiments, there is provided a method of degrading a polysaccharide, such as a glycosaminoglycan, by contacting the glycosaminoglycan with a mutant ChABC (or a modification or variant thereof) or composition, as provided herein, in an amount effective to degrade the glycosaminoglycan. Such a method can be an in vitro or in vivo method. In one example, the mutant ChABC can be used for digestion of glycans in vitro, during analysis, detection and/or quantification of protein glycosylation (e.g., as a reagent for in vitro glycomics (Sethi, 2020, *Mol. Omics.* 16, 364-376)).

Alternatively, the compositions and mutant ChABC enzymes provided herein can be used in a method of treatment. For such uses, the pharmaceutical composition, mutant ChABC or polynucleotide, vector or host cell expressing the mutant ChABC, can be formulated for different routes of administration using methods well known to those skilled in the art. For example, the pharmaceutical composition or mutant ChABC can be formulated for oral administration, or, preferably, parenteral administration. In particular, routes of administration include, but are not limited to: intradermal, intramuscular, intraperitoneal, intravenous, subcutaneous, intranasal, epidural, sublingual, intranasal, intracerebral, intravaginal, rectally, by inhalation, orally, or topically. The mode of administration can be left to the discretion of the practitioner, and depends in-part upon the site of the medical condition in the subject.

The mutant ChABC, or polynucleotide, vector or host cell expressing the mutant ChABC, and compositions thereof, are useful for a variety of purposes, including degrading and/or analyzing polysaccharides such as glycosaminoglycans (GAGs). These GAGs can include, but are not limited to, chondroitin sulfate, dermatan sulfate and heparin sulfate proteoglycans. The mutant ChABC enzymes can also be used in therapeutic methods for treating conditions associated with excess proteoglycan formation or conditions for which treatment is benefitted by degradation of proteoglycans, such as, but not limited to, promoting nerve regeneration, promoting stroke recovery, treating spinal cord injury, treating epithelial disease, treating infections, treating fibrosis, treating scars.

The mutant ChABC, or polynucleotide, vector or host cell expressing the mutant ChABC, and compositions thereof, can also be used for treating cancer (alone or in combination with other chemotherapeutic agents) in manner similar to what has been described in relation to wild-type ChABC (see, e.g., US 2007/0148157, US 2007/0224670, WO 2005/087920, Jaime-Ramirez A. et al., *Neuro Oncol.* 2014 November; 16(Suppl 5): v161., and Jaime-Ramirez A. C. et al., *J Gene Med* 2017 January: 19(3) ee2942, each of which is incorporated by reference herein in its entirety)

For example, the mutant ChABC can be used in the treatment of diseases or disorders characterised by over production of proteoglycans. For example, the mutant ChABC, or polynucleotide, vector or host cell expressing the mutant ChABC, and compositions thereof can be used to treat scarring or fibrosis disease that involves CS or DS deposition, including, without restriction, in the CNS, in cardiac fibrosis (Zhao, et al., 2018, *Circulation* 137 (23), 2497-2513), pulmonary fibrosis (Venkatesan et al., 2011, *Am J Physiol Lung Cell Mol Physiol.* 300(2) L191-L203), or fibrotic renal diseases (Lensen, et al., 2015, *PLoS ONE* 10(8): e0134946).

In other embodiments there is provided a method for promoting nerve regeneration in a subject in need thereof. In one embodiment the nerve regeneration is axon regeneration. In one embodiment the method is directed to the treatment of a subject that has had a central nervous system injury. In another embodiment the subject has had a spinal cord injury. In another embodiment the subject has a neurodegenerative disorder. In yet a further embodiment the subject has had a stroke.

To gain a better understanding of the invention described herein, the following examples are set forth. It should be understood that these examples are for illustrative purposes only. Therefore, they should not limit the scope of this invention in any way.

EXAMPLES

Example 1

Materials and Methods

Prediction of Stabilized Chondroitinase ABC-SH3 Mutations

Using the PROSS protocol,[1] stabilizing mutations were predicted for an apo structure of ChABC from *Proteus vulgaris* (Uniprot entry: CABC1_PROVU): chain A of PDB 1HN0,[2] solved using X-ray diffraction to a resolution of 1.9 Å. The structure has 1021 residues, with three adjacent domains Lyase_N-lyase_catalyt-Lyase_8, as identified by Pfam 31.0.[3]

The method constructs a multiple-sequence alignment from sequences in the NCBI non-redundant database (nr) with BlastP E-value of less than 1e-4 to the query.[4] The sequences were then aligned using MUSCLE[5] with the default parameters. Homologues with insertions or deletions in DSSP-labeled loops[6] were removed, yielding 70 sequences with a minimum and median percent coverage of 59.4% and 92.2%, and minimum and median percent sequence identity of 23.5% and 41.7% (Supplemental FIG. 2). A position-specific scoring matrix (PSSM) was then computed using PSI-BLAST,[7] giving the log probability of each amino acid at each position. Amino acids at positions with a PSSM score ≤0 were rejected. To bias towards mutations that independently provide stability, for each candidate point mutation at each position, the wild-type structure was optimized using the Rosetta mutational scanning protocol[8] which repacks sidechains within 8A of the candidate point mutation and globally minimizes all torsion angles using the Talasis2014 weight set combined with a native-coordinate constraint with weight 0.5 and a Boltzmann PSSM constraint weight of 1. The mutational scanning protocol rejects candidate point mutations if the predicted change in free energy ($\Delta\Delta G_{calc}$) was not less than −1.8, −1.25, or −0.45 Rosetta Energy Units (REU) for the three final designs: ChABC-37-SH3, ChABC-55-SH3, and ChABC-92-SH3, respectively. Then for each energy level, the wild type and remaining mutations were jointly considered using a protocol that applies the following sequence of movers: soft_design, soft_min, soft_design, hard_design, hard_min, hard_design, hard_min, hard_design, RT_min, RT_min, hard_min. The movers with the soft prefix use soft_rep weight set, which dampens repulsive van der waals forces, and those with the hard prefix use the Talaris2014 weight sets. The 'design' movers design and repack the sidechain amino acid type and torsion angles while keeping the backbone fixed whereas the 'min' movers minimize all torsion angles. The 'RT_min' mover does rotamer trials, which sequentially considers each rotamer at each position without design. The design stage uses a constraint weight of 0.4 for the native sequence and 0.4 for the PSSM profile. General Rosetta flags were:

- -ex1, -ex2, -use_input_sc, -extrachi_cutoff 5, -ignore_unrecognized_res, -use_occurrence_data, -linmem_ig 10, -ignore_zero_occupancy false, -restore_talaris behavior.

Assembly of Mutant Chondroitinase ABC-SH3 Constructs

The mutant ChABC sequences were based on the original ChABC sequence (Protein Data Bank Structure 1HN0) and are set out below.

```
Original ChABC Sequence
(Protein Data Bank Structure: 1HN0)
                                          SEQ ID NO: 1
MPIFRFTALAMTLGLLSAPYNAMAATSNPAFDPKNLMQSEIYHFAQNNPL

ADFSSDKNSILTLSDKRSIMGNQSLLWKWKGGSSFTLHKKLIVPTDKEAS

KAWGRSSTPVFSFWLYNEKPIDGYLTIDFGEKLISTSEAQAGFKVKLDFT

GWRAVGVSLNNDLENREMTLNATNTSSDGTQDSIGRSLGAKVDSIRFKAP

SNVSQGEIYIDRIMFSVDDARYQWSDYQVKTRLSEPEIQFHNVKPQLPVT

PENLAAIDLIRQRLINEFVGGEKETNLALEENISKLKSDFDALNIHTLAN

GGTQGRHLITDKQIIIYQPENLNSQDKQLFDNYVILGNYTTLMFNISRAY

VLEKDPTQKAQLKQMYLLMTKHLLDQGFVKGSALVTTHHWGYSSRWWYIS

TLLMSDALKEANLQTQVYDSLLWYSREFKSSFDMKVSADSSDLDYFNTLS

RQHLALLLLEPDDQKRINLVNTFSHYITGALTQVPPGGKDGLRPDGTAWR

HEGNYPGYSFPAFKNASQLIYLLRDTPFSVGESGWNNLKKAMVSAWIYSN

PEVGLPLAGRHPFNSPSLKSVAQGYYWLAMSAKSSPDKTLASIYLAISDK

TQNESTAIFGETITPASLPQGFYAFNGGAFGIHRWQDKMVTLKAYNTNVW

SSEIYNKDNRYGRYQSHGVAQIVSNGSQLSQGYQQEGWDWNRMEGATTIH

LPLKDLDSPKPHTLMQRGERGFSGTSSLEGQYGMMAFNLIYPANLERFDP
```

```
-continued
NFTAKKSVLAADNHLIFIGSNINSSDKNKNVETTLFQHAITPTLNTLWIN

GQKIENMPYQTTLQQGDWLIDSNGNGYLITQAEKVNVSRQHQVSAENKNR

QPTEGNFSSAWIDHSTRPKDASYEYMVFLDATPEKMGEMAQKFRENNGLY

QVLRKDKDVHIILDKLSNVTGYAFYQPASIEDKWIKKVNKPAIVMTHRQK

DTLIVSAVTPDLNMTRQKAATPVTINVTINGKWQSADKNSEVKYQVSGDN

TELTFTSYFGIPQEIKLSPLP
```

Point Mutations in ChABC Sequences

Design 1: 37 Mutations

- SER 68 TYR
- LEU 76 GLN
- GLY 81 ALA
- LYS 90 PRO
- SER 107 ALA
- ILE 134 ASN
- VAL 155 CYS
- LEU 233 TYR
- GLU 235 VAL
- LYS 244 GLU
- ILE 257 VAL
- ALA 278 LYS
- LEU 308 ILE
- ILE 314 LYS
- ASN 321 HIS
- SER 324 PRO
- ASN 338 ASP
- SER 347 ALA
- GLU 353 ASN
- SER 393 ASN
- THR 401 ALA
- ALA 438 PRO
- LYS 465 GLU
- VAL 470 LEU
- ASN 471 HIS
- SER 517 ALA
- LYS 583 PRO
- ASN 656 HIS
- ASN 675 TYR
- GLN 685 GLU
- GLU 694 PRO
- LYS 704 ASP
- ARG 720 THR
- GLN 831 GLU
- GLY 887 GLN
- MET 889 TYR
- GLY 898 ARG

Design 2: 55 Mutations

- SER 68 TYR
- LEU 76 GLU
- GLY 81 ALA
- LYS 90 PRO
- SER 107 ALA
- ILE 134 ASN
- VAL 155 ILE
- SER 204 LYS
- GLU 207 ARG
- TYR 209 PHE
- LEU 233 TYR
- GLU 235 VAL
- GLN 239 ASP
- LYS 244 GLU
- GLN 246 LEU

VAL 249 ALA
ILE 257 VAL
ALA 278 LYS
LEU 308 ILE
ILE 314 LYS
ASN 321 HIS
SER 324 PRO
ASN 338 ASP
SER 347 ALA
GLU 353 ASN
SER 393 ASN
THR 401 ALA
SER 437 GLY
ALA 438 PRO
LYS 465 GLU
VAL 470 LEU
ASN 471 HIS
SER 517 ALA
ASN 536 GLN
LYS 583 PRO
ALA 596 ARG
THR 606 GLU
ALA 644 GLY
ASN 656 THR
ASN 675 TYR
GLN 685 GLU
GLU 694 PRO
LYS 704 ASP
LYS 710 ASN
ARG 720 THR
ASN 806 THR
GLN 814 THR
GLN 831 GLU
THR 866 ARG
GLY 887 LYS
MET 889 TYR
GLY 898 LYS
LEU 913 LYS
SER 929 GLU
SER 1018 LYS

Design 3: 92 Mutations

LYS 34 ASN
SER 68 TYR
LEU 76 GLU
GLY 81 ALA
THR 86 VAL
LYS 90 PRO
VAL 93 ILE
SER 106 PRO
SER 107 ALA
THR 126 ARG
ILE 134 ASN
ASP 148 ASN
VAL 155 CYS
SER 204 LYS
GLU 207 ARG
TYR 209 PHE
LEU 233 TYR
GLU 235 VAL
GLN 239 ASP
LYS 244 GLU
GLN 246 LEU
LEU 247 PRO
ILE 257 VAL
LEU 259 THR
ASN 266 ASP
VAL 269 ALA
ALA 278 LYS
SER 284 ASP
ASP 289 LYS
ASN 300 ASP
LEU 308 ILE
ILE 314 LYS
ASN 321 HIS
SER 324 ALA
ASN 338 ASP
SER 347 ALA
VAL 351 TYR
GLU 353 ASN
SER 393 ASN
THR 401 ALA
THR 415 GLN
SER 437 GLY
ALA 438 PRO
ASP 442 ASN
LYS 465 GLU
ASN 471 HIS
SER 517 ALA
SER 529 GLU
ASN 536 GLN
LYS 583 PRO
SER 592 ALA
ALA 596 ARG
ASP 599 GLY
THR 606 LYS
GLN 636 GLY
ALA 644 GLY
THR 647 LYS
ASN 656 THR
VAL 669 THR
ASN 675 TYR
LEU 679 LYS
GLN 685 GLU
GLU 686 ASN
GLU 694 PRO
LYS 704 GLU
ASP 705 GLU
LYS 710 ASN
ARG 720 THR
ILE 740 GLN
ALA 743 GLN
GLU 746 PRO
LYS 779 TYR
GLU 805 THR
ASN 806 GLN
GLN 814 GLY
GLN 831 GLU
VAL 843 THR
GLU 846 ASP
THR 866 ARG
ASP 870 ASN
GLY 887 LYS
MET 889 TYR
GLY 898 LYS
LEU 913 HIS
SER 929 GLU
LYS 940 ARG
THR 952 ILE
VAL 958 SER
THR 971 LYS
ASN 980 LYS
GLU 1002 VAL
SER 1018 LYS

Mutant ChABC amino acid sequences were codon optimized for *E. coli* gene expression using the IDT DNA codon optimization web tool. Gene sequences were purchased from TWIST Bioscience (San Francisco, CA) as two halves containing 1,499 and 1,603 base pairs, and each was cloned into the pTWIST standard vector using AscI, DraI, and XhoI (New England Biolabs, Ipswich, MA). The pieces of each design were cut from the pTWIST vector, and both halves were ligated and inserted into a pET28b$^+$ vector containing a kanamycin resistance cassette after the isopropyl β-D-1-thiogalactopyranoside (IPTG)-inducible T7 promoter between the existing hexahistidine (HHHHHH) and FLAG (DYKDDDDK) tags. The complete sequences read as follows: hexahistidine tag, SH3 domain, flexible linker, ChABC, and FLAG tag. Plasmids were cloned into NEB5-α High Efficiency competent cells (New England Biolabs, Ipswich, MA) and validated by Sanger sequencing (ACGT Corporation, Toronto, ON).

Chondroitinase ABC-SH3 Expression and Purification

Mutant ChABC-SH3 was expressed and purified as previously described for ChABC-SH3.[9] Plasmids were transformed into NiCo21 (DE3) *E. coli* cells for protein expression (New England Biolabs). For small-scale verification of protein expression from single colonies, cells were grown overnight at 37° C. in 10 mL of Luria Bertani (LB) broth supplemented with 50 μg/ml of kanamycin, followed by induction of protein expression with 0.8 mM IPTG during the log phase of growth ($OD_{600nm}$≥0.8) for an additional 5 h. Cell cultures were centrifuged, treated with BugBuster® Protein Extraction Reagent (Millipore Sigma, Burlington, MA) for bacterial lysis, and centrifuged again to separate the soluble and insoluble fractions. The soluble fraction of the bacterial lysate was denatured and separated by mass using sodium dodecyl sulfate polyacrylamide gel electrophoresis (SDS-PAGE) followed by Coomassie Brilliant Blue staining for non-specific staining of all protein bands.

For large-scale protein production, NiCo21 cells were grown overnight at 37° C. in 20 mL of LB broth with 50 μg/ml of kanamycin and then transferred to 1.8 μL of Terrific Broth (TB) supplemented with 0.4% glycerol, 50 μg/ml of kanamycin, and 500 μL of anti-foaming agent (Antifoam 204™). TB cultures were grown at 37° C. in a LEX-10 bubbler system (Epiphyte3, Toronto, ON) with constant air sparging until $OD_{600nm}$≥0.8 was reached, upon which 0.8 mM IPTG was added and protein expression was allowed to proceed at 22° C. for 18 hours. TB cultures were centrifuged for 15 min at 6000 rpm and 4° C. (Avanti™ JXN-26 centrifuge, Beckman Coulter, Brea, CA). Cell pellets were resuspended in 40 mL of lysis buffer (50 mM Tris pH 7.5, 500 mM NaCl, 5 mM imidazole) and lysed using a 500 W sonicator (QSonica™, Newtown, CT) at 30% amplitude for 5 min at 10 s intervals. The soluble fraction of the cell lysate was incubated with 1.8 mL of nickel-nitrilotriacetic acid (Ni-NTA) resin for 15 min at 4° C. to promote binding between the nickel and hexahistidine tag on ChABC-SH3. The cell lysate was poured through a glass chromatography column, and the Ni-NTA resin was washed with 10×10 mL of wash buffer (50 mM Tris pH 7.5, 500 mM NaCl, 30 mM imidazole). Nickel-bound proteins were eluted using a high concentration of imidazole (40 mM Tris pH 7.5, 500 mM NaCl, 250 mM imidazole), and subsequently incubated with 5 mL of pre-washed chitin resin (New England Biolabs) in elution buffer for 1 hour. The solution was poured through another glass chromatography column and concentrated to 1-2 mL with a 10,000 kDa cut-off Vivaspin® 20 centrifugal concentrator (Sartorius, Gottingen, Germany). Size exclusion chromatography was performed using a Hi-load® 16/600 Superdex® 200 column on an AKTA Purifier 10 (GE Healthcare Life Sciences, Budapest, Hungary) in 50 mM sodium acetate, 10 mM phosphate buffer (pH 8.0). Ten consecutive 1 mL fractions, corresponding to unaggregated protein based on 280 nm signal and time of elution from the Superdex® 200 column, were collected and concentrated to ~1-2 mL with a centrifugal concentrator. Purified ChABC-SH3 was filter-sterilized (Amicon Ultrafree-MC 0.22 μm Centrifugal Filter Units, Millipore Sigma) and stored in 50 mM sodium acetate in phosphate-buffered saline (PBS) (pH 8.0) at −80° C. until use. Protein concentration was quantified by measuring sample absorbance at 280 nm using the molecular weight (125 kDa) and extinction coefficient (211,000 $M^{-1}$ $cm^{-1}$) of ChABC-SH3.

Circular Dichroism

For circular dichroism readings, proteins were diluted to 0.2 mg/mL in PBS (pH 7.4), and 150 μL were pipetted into a glass cuvette with a path length of 1 cm. The far-UV (200-260 nm) circular dichroism spectra of ChABC-SH3 and mutants were measured using a JASCO J-810 circular dichroism spectrophotometer (JASCO, Easton, MD) and expressed as molar ellipticity (deg $cm^2$ $dmol^{-1}$). Alpha helix and beta sheet content was determined via deconvolution using Dichroweb.[10]

Static Light Scattering

Proteins were diluted to 1 mg/mL in PBS (pH 7.4) and 9 μL were pipetted into glass capillaries for static light scattering (SLS) (UNit, Unchained Labs, Pleasanton, CA). SLS readings were taken at 466 nm between 25 and 70° C. using a temperature scan rate of 1° C./min to evaluate protein unfolding and subsequent aggregation. Melting temperatures ($T_m$) were determined using Boltzmann regression for the midpoint of the linear denaturation curve.

Chondroitinase ABC-SH3 Activity

The enzymatic activity of ChABC-SH3 was evaluated by measuring the degradation of the substrates, chondroitin sulfate A or dermatan sulfate, which exhibit an absorbance change at 232 nm following cleavage by chondroitinases. 10 μL of 0.1 mg/mL ChABC-SH3 was mixed with 90 μL of 10 mg/mL chondroitin sulfate A or dermatan sulfate in a UV-Star® microplate (Greiner Bio-One™, Monroe, NC) and immediately read on a plate reader (Tecan Infinite M200 Pro™) at 232 nm. Readings were taken at room temperature every 20 s for 20 min, and the slope of the resultant linear relationship between absorbance and time was used to calculate the kinetic activity of ChABC-SH3 in units of activity (mmol substrate degraded per min) per mg of protein (U/mg). To evaluate long-term enzymatic activity, solutions of 0.1 mg/mL of ChABC-SH3 in PBS (pH 7.4) with 0.1% (w/v) bovine serum albumin (BSA) and protease inhibitor tablets (cOmplete Mini™ Protease Inhibitor Cocktail, Roche, Switzerland) were incubated at 37° C. for up to 7 days and then frozen at −80° C. until analysis. The half-life of active ChABC-SH3 was calculated by fitting activity data over time to a one-phase exponential decay curve, and the area under the activity curve (AUC) over 7 days was calculated using the trapezoid rule.

Kinetic parameters for chondroitin sulfate A and dermatan sulfate were determined using the initial rates of product formation when 10 μL of 0.1 mg/mL ChABC-SH3 were mixed with 90 μL of 1-10 mg/mL substrate. Data were fit to the Michaelis-Menten equation, and $V_{max}$, $K_m$, and $k_{cat}$ were determined by non-linear regression using Graphpad Prism™.

Proteolytic Degradation

Proteolysis was carried out as detailed by Kheirollahi et al, 2017.[11] Briefly, wild type and mutant ChABC-SH3 (0.4 mg/mL) were incubated with trypsin (2 μg/mL) in 20 mM Tris buffer containing 10 mM $CaCl_2$ at pH 7.5 at room temperature. The reaction was inhibited with 1 mM phenylmethylsulfonyl fluoride (PMSF) after 45 minutes. Proteins were denatured and separated by SDS-PAGE, followed by Coomassie Brilliant Blue staining. Specific activity for chondroitin sulfate A was measured as detailed above. Specific activity was compared to ChABC-SH3 that had been incubated in buffer without trypsin for 45 minutes at room temperature.

Affinity Release of ChABC-SH3 from Methylcellulose Hydrogels

Cross-linked methylcellulose hydrogels for affinity-controlled release of ChABC-SH3 were fabricated as previously described.[12,13] Briefly, 100 μL of 5% (w/v) methylcellulose containing 20 μg of ChABC-SH3 or ChABC-37-SH3 and 0.1 μmol of thiol were cross-linked with 3000 Da PEG-bismaleimide crosslinker at a ratio of 0.75:1 maleimide to thiol. To control release, binding peptides for the SH3 domain of the fusion protein (KPPVVKKPHYLS) with a dissociation constant of $2.7\times10^{-5}$ M were incorporated into the hydrogel at 100 times molar excess to the protein. Hydrogels were speed-mixed into solution (SpeedMixer™ DAC 150 FV2, FlackTek, Landrum, SC), cross-linked, and incubated at 4° C. overnight prior to incubation in 400 μL of PBS (pH 7.4) with 0.1% (w/v) BSA and protease inhibitors for 7 days at 37° C. PBS was removed and replaced at 0 h, 2 h, 6 h, and 1, 2, 4, and 7 d. ChABC-SH3 and ChABC-37-SH3 release was quantified using a custom enzyme-linked immunosorbent assay (ELISA) as previously described.[9] Activity for chondroitin sulfate A was quantified and normalized to protein release.

Statistical Analysis

All data are reported as mean±standard deviation. In vitro experiments were performed with a minimum of 3 biological replicates for each experimental group. Statistical significance was determined using one-way or two-way ANOVA as appropriate, followed by Bonferroni's post hoc analysis (Graphpad Prism™, Version 7.0, La Jolla, CA). $p<0.05$ was considered statistically significant. One-phase exponential decay and Michalis-Menten curve fitting, as well as AUC determination, were also performed using Graphpad Prism™

Sequence Analysis

Sequence conservation for ChABC shown in Supplemental FIG. 2 is computed as the sum of pairwise scores for all wild type positions of the alignment computed by msaConservationScore (BLOSUM64) from the R msa package,[14] and smoothed using the loess method from the R stats package,[15] with span=0.05 Domain structure was defined by Pfam 31.0.[16] Secondary structure was defined from the dictionary of protein secondary structure (DSSP) codes.[6] Supplemental FIG. 2 was generated using the R the ggplot2 package.[17]

Structure Analysis

FIGS. 3, 6 and 7 were generated using PyMOL.[18]

Results and Discussion

Stabilizing proteins through mutagenesis is challenging because most mutations are destabilizing, and those that are stabilizing, typically make only a minor impact on overall protein stability. Furthermore, for large proteins like ChABC, deep mutational scanning can only explore a fraction of the sequence space.[39] To meet this challenge, the present inventors leveraged the consensus effect hypothesis, in combination with computational protein design—an approach that has been successful in stabilizing other biocatalysts.[40,41] The consensus hypothesis proposes that the amino acids most frequently observed in nature increase stability,[42] because amino acids that disrupt structure and function are evolutionarily disfavored[43] and ancestral proteins are typically more thermally stable.[44] Starting with the 1.9 Å X-ray crystal structure for ChABC enzyme from *P. vulgaris* (1HN0),[45] the Protein One Stop Shop (PROSS) method[40] was used, which predicts the stability of all mutations at each position using Rosetta local conformation sampling and energetic scoring with a sequence conservation bias from a multiple sequence alignment of 71 extant ChABC enzymes (FIG. 1). Using three separate energy thresholds, it combined all independently stabilizing mutations in a global optimization of structure and sequence (Methods, Predictions of Stabilized ChABC-SH3 Mutations) yielding mutant sets (FIG. 2) containing 37, 55, and 92 cumulative mutations (FIG. 3). The DNA sequences were codon-optimized for expression in *E. coli*. All mutants maintained close agreement with 1HN0 and demonstrated lower predicted folding free energies than the wild type enzyme when globally relaxed in Rosetta, indicative of increased stability (FIG. 4).

Interestingly, PROSS maintained amino acids at or near conserved active site residues (H501, Y508, R560 and Q653)[8] and at metal binding residues (D442, D444, and Y392)[46] highlighting the value of consensus design. Further, individual mutations predicted by PROSS employed established stabilization strategies, such as introducing charge-charge interactions,[47] and rigidifying loops and helices through side-chain H-bonds and backbone prolines[27,48] (FIG. 5). Simultaneously mutating dozens of residues increases the risk of introducing a highly destabilizing mutation, but opens the opportunity for multiple weak stabilizing mutations to lead to a significant overall stabilizing effect.[49] The majority of mutations were novel, with only 4 overlapping with the 46 previously mutated residues (Table 1, FIG. 6).

N-terminal SH3 fusions of each design (i.e., ChABC-SH3, FIG. 7) were expressed in NiCo21 (DE3) *E. coli* cells to enable controlled release from a hydrogel containing SH3 binding peptides.[50] Expressed proteins were purified using a nickel affinity column for the hexahistidine tag on the protein followed by size exclusion chromatography. Gel electrophoresis and staining demonstrate that each design was expressed at the correct molecular weight (125 kDa) with minimal other contaminating proteins (FIG. 8A). Large-scale (2 L) cultures of designs resulted in 3.5-fold more protein than wild type (FIG. 8B), under the same protein expression and purification protocols, reflecting better functional protein production overall.

Circular dichroism revealed that mutants did not significantly disrupt protein structure (FIG. 9A), with similar alpha helix and beta sheet composition between wild type (alpha helix: 32%, beta sheet: 16%) and mutants (ChABC-37-SH3: alpha helix: 32%, beta sheet: 16%; ChABC-55-SH3: alpha helix: 32%, beta sheet: 17%; ChABC-92-SH3: alpha helix: 31%, beta sheet: 17%). Mutant stability was evaluated by measuring protein aggregation under a 1° C./min temperature increase (FIG. 9B). The mutant aggregation temperatures increased by between 4 and 8° C. relative to wild type (ChABC-SH3: 49° C.; ChABC-37-SH3: 55° C.; ChABC-55-SH3: 57° C.; ChABC-92-SH3: 57° C.), matching or exceeding the shifts of other ChABC mutants that maintained full enzymatic activity (Table 1).

Since ChABC degrades both CS and DS substrates,[45,51] it may synergistically stimulate tissue regeneration by both decreasing glial scar formation through DS degradation and increasing axonal regrowth into the injury site through CS degradation.[52] Only ChABC-37-SH3 exhibited higher initial enzymatic activity against both CS and DS compared to wild type, whereas ChABC-55-SH3 and ChABC-92-SH3 exhibited significantly lower activity (FIG. 10A, FIG. 11). Although the activity of all ChABC proteins for CS decreased over time, this decrease was slower for mutant proteins than the wild type (FIG. 12). Only ChABC-37-SH3 remained significantly active (>16 U/mg) after 7 days at 37° C., while the wild type and other mutant proteins exhibited less than 3 U/mg of activity after 7 days (FIG. 10A). Designed chondroitinases demonstrated drastically higher functional half-lives (50% of initial activity: 3.2-6.3 days) compared to ChABC-SH3 (0.7 days) (FIG. 10B). However, only ChABC-37-SH3 significantly increased total CS degradation (FIG. 10C). Estimated kinetic parameters ($k_{cat}$, $V_{max}$) of ChABC-37-SH3 were significantly higher than those of ChABC-55-SH3 and ChABC-92-SH3 (Table 2, FIG. 13), further demonstrating the increased efficacy of ChABC-37-SH3 compared to the other designed mutants. Additionally, the low overall activity of ChABC-55-SH3 for CS resulted in a poor fit ($R^2$=0.87) of the Michaelis-Menten curve compared to all other enzymes ($R^2 \geq 0.93$), yielding enzymatic parameters with high standard deviations (Table 2).

To achieve sustained release of the designs using an injectable, affinity-controlled hydrogel delivery system,[50,53] ChABC-37-SH3 and ChABC-SH3 were separately incorporated in 5% (w/v) thiolated methylcellulose hydrogels cross-linked with PEG bismaleimide, with or without SH3 binding peptides (100:1 molar ratio of peptide to protein) (FIG. 15A). Protein release into artificial cerebrospinal fluid (aCSF) was measured over 7 days using a custom-designed enzyme-linked immunosorbent assay (ELISA) to detect the hexahistidine and FLAG tags expressed on the enzymes. Hydrogels containing SH3 binding peptides reduced protein release at 2, 4, and 7 days compared to hydrogels without binding peptides (FIG. 15B), and ~20% of the ChABC-37-SH3 loaded into MC-peptide gels was released between days 2 and 7, confirming that sustained protein release via the SH3 binding domain could be achieved with both the wild type and mutant proteins. Released ChABC-37-SH3 demonstrated better long-term proteolytic activity than the wild type enzyme over 7 days (FIG. 15C), demonstrated by significant differences in enzymatic activity of the supernatant at 1 and 2 days (FIG. 16) and an increased area under the activity curve (FIG. 15D).

Although all mutants were more stable and displayed increased proteolytic resistance compared to wild-type

TABLE 2

Michaelis-Menten kinetic parameters of ChABC-SH3 designs (n = 3, mean ± SD)

| | Chondroitin Sulfate A | | | | | Dermatan Sulfate | | | | |
|---|---|---|---|---|---|---|---|---|---|---|
| Protein | $K_M$ (μM) | $V_{max}$ (μM $min^{-1}$) | $k_{cat}$ ($min^{-1}$) | $k_{cat}/K_M$ (μ$M^{-1}$ $min^{-1}$) | $R^2$ | $K_M$ (μM) | $V_{max}$ (μM $min^{-1}$) | $k_{cat}$ ($min^{-1}$) | $k_{cat}/K_M$ (μ$M^{-1}$ $min^{-1}$) | $R^2$ |
| ChABC-SH3 | 2132 ± 467 | 392 ± 18 | 4894 ± 230 | 2.30 ± 0.51 | 0.94 | 2175 ± 291 | 365 ± 11 | 4560 ± 140 | 2.10 ± 0.29 | 0.98 |
| ChABC-37-SH3 | 2821 ± 657 | 387 ± 23 | 4840 ± 293 | 1.72 ± 0.41 | 0.93 | 3655 ± 565 | 461 ± 21 | 5759 ± 261 | 1.58 ± 0.25 | 0.98 |
| ChABC-55-SH3 | 16180 ± 12149 | 64 ± 27 | 802 ± 334 | 0.05 ± 0.04 | 0.87 | 4778 ± 530 | 222 ± 18 | 2776 ± 102 | 0.58 ± 0.07 | 0.99 |
| ChABC-92-SH3 | 2120 ± 445 | 140 ± 7 | 1753 ± 83 | 0.83 ± 0.18 | 0.94 | 3297 ± 1091 | 298 ± 28 | 3722 ± 344 | 1.14 ± 0.39 | 0.90 |

All mutant proteins also displayed higher resistance to proteolytic degradation (FIG. 14). After incubation with 2 g/mL of trypsin for 45 minutes, mutant ChABC-SH3 displayed a higher proportion of intact protein (125 kDa band) compared to wild type ChABC-SH3 (FIG. 14A). Furthermore, impressively, all mutant proteins retained 100% of their original activity following trypsin treatment, while wild type ChABC-SH3 only retained 31% of its original activity (FIG. 14B). Without wishing to be bound by theory, this may be due to mutations causing conformational changes in the protein structure, thereby increasing protein rigidity or decreasing accessibility to basic residues typically cleaved by trypsin.[23]

Stabilization via mutagenesis often leads to decreased catalytic efficiency ($k_{cat}/K_m$). For example, H700N/L701T, the most stabilizing mutation to date,[25] has an aggregation temperature 16° C. greater than wild type ChABC but is 40% less catalytically efficient. In contrast, ChABC-37-SH3 has an aggregation temperature 6° C. greater than wild type, is more active overall, and is only 25% less catalytically efficient for CS (Table 2). Thus, ChABC-37-SH3 is particularly attractive for further development.

ChABC-SH3, only one design (ChABC-37-SH3) demonstrated the desired increase in both stability and enzymatic activity towards CS and DS. This indicates that, while PROSS successfully predicted increased protein structural stability, it could not reliably predict enzymatic activity. Without wishing to be bound by theory, it is suggested that mutations that reduced enzymatic activity may interfere with other functionally relevant states that facilitate substrate binding to the active site, thereby reducing the catalytic efficiency (Table 3). This is supported by the high $K_m$ (or low substrate affinity) of ChABC-55-SH3 compared to the other enzymes (Table 2). A similar effect was observed by Shirdel et al., where structurally stabilized ChABC mutants demonstrated lower enzymatic efficiency; this was attributed to a decrease in flexibility of the protein, since substrate binding typically results in a conformational change.[25] Notably, increasing the number of mutations did not necessarily lead to decreased function. ChABC-92-SH3 (FIG. 3C), which included an additional 37 unique mutations to 55 changes already in ChABC-55-SH3 (FIG. 3B), demonstrated higher initial activity, indicating that additional stabilizing mutations can counteract destabilizing mutations and rescue lost enzymatic activity.

TABLE 3

Sequence Co-variation. Sequence co-variation for ChABC was evaluated by building a deep multiple sequence alignment for ChABC using DeepMeta (Wu, et al., 2019, Bioinformatics), which iteratively searches two large meta-genome databases using a HMM-profile based strategy. This yielded 1851 sequences with an average sequence depth of 683 over 607 positions. Using this alignment, a Markov-random-field model was fit capturing the 1-body and 2-body terms using the pseudo-log-likelihood based method GREMLIN.[21] Evaluating the log-likelihood ratio for each design relative to the wild type under the model shows that the increasing permissive energy thresholds in PROSS yields sequences with better 1-body energies, consistent with the consensus bias, but worse 2-body energies (Supplemental Table 2). This suggests that the PROSS method is not capturing evolutionarily relevant sequence co-variation in its designs. This missing co-variation effect may be due to contacts that form in one or more alternative, functionally relevant states, not captured by the X-ray, which may explain why the ChABC-SH3-55 and ChABC-SH3-92 designs were more stable but less active.

Log probability of designs relative to wild type under GREMLIN MRF model (larger is better)

| | Total | 1-Body | 2-Body |
|---|---|---|---|
| ChABC-SH3-37 | −22.2 | 9.47 | −31.7 |
| ChABC-SH3-55 | −27.0 | 15.2 | −42.2 |
| ChABC-SH3-92 | −33.3 | 24.6 | −58.0 |

Given the high likelihood of destabilizing mutations that reduce enzyme activity, the success of ChABC-37-SH3 with 37 mutations highlights the value of integrating both evolutionary data and native state energy optimization into a single approach.[40,41] Unlike other efforts to stabilize ChABC, which focused on optimizing specific aspects of the protein structure with point mutations,[11,21-32] PROSS considers all possible amino acid changes biasing towards those that independently contribute stability and are often observed at the given position. The fact that 71 ChABC variants are naturally occurring in a variety of bacteria species (FIG. 1) provides ample evolutionary data to increase the predictive power of this approach. The use of PROSS to generate ChABC-37-SH3, with 3.5 times higher protein yield, a 6.5 times greater functional half-life, and 6° C. increase in aggregation temperature with no loss of enzymatic activity, demonstrates the significant advantage of this strategy compared to traditional site-directed mutagenesis. ChABC-37-SH3 exhibits the highest long-term activity and total substrate degradation of any documented wild type or modified form of ChABC. Moreover, the dramatic improvement in proteolytic resistance demonstrated by all mutants has never before been documented.

Widespread use and commercialization of ChABC have been hampered by its thermal instability, limited activity, and poor sustained, local delivery. The re-engineered ChABC mutant, ChABC-37-SH3, overcomes these challenges by significantly extending the bioactive lifespan of the enzyme and enabling sustained release from a hydrogel via the SH3 fusion domain. Considering the fragile nature of this protein, a hydrogel that maintains protein bioactivity will significantly improve the feasibility of its clinical use. Unlike traditional protein encapsulation in polymeric biomaterials, which typically decreases protein activity and loading, this affinity-based delivery strategy maintains ChABC activity at levels similar to that of soluble protein (FIG. 10A, 15C). Furthermore, it is expected that degradation of CSPGs using ChABC-37-SH3 will promote axonal outgrowth in the CNS, based on previous reports of axonal outgrowth stimulated by both wild-type ChABC[17,54,55] and ChABC-SH3 fusion protein[16] delivery.

While the presently tested affinity-based delivery strategy only resulted in release of ~62% of the loaded ChABC-37-SH3 over 7 days in vitro, full protein release is expected to be achieved in vivo due to gradual breakdown of the hydrogel. A significant portion of the loaded protein (~20%) is released at later time points, between days 2 and 7, which is expected to promote long-term effects. In previous studies, a prolonged effect of ChABC-SH3 was observed when delivered using this strategy for up to 2 weeks and 4 weeks in the spinal cord and brain, respectively. The methylcellulose delivery vehicle can be further engineered to facilitate expedited degradation and resorption in vivo.

The modifications to ChABC described herein have improved its production, stability, and long-term bioactivity, overcoming many challenges required for clinical translation and facilitating its future use as a viable therapeutic in treating CNS injuries. More broadly, this first demonstration of the use of PROSS to optimize a therapeutic agent, such as ChABC, highlights the versatility of this method as an approach for optimizing particularly sensitive proteins.

REFERENCES (1) Hamai, A.; Hashimoto, N.; Mochizuki, H.; Kato, F.; Makiguchi, Y.; Horie, K.; Suzuki, S. Two Distinct Chondroitin Sulfate ABC Lyases: AN ENDOELIMINASE YIELDING TETRASACCHARIDES AND AN EXOELIMINASE PREFERENTIALLY ACTING ON OLIGOSACCHARIDES. *J. Biol. Chem.* 1997, 272 (14), 9123-9130.

(2) Silver, J.; Miller, J. H. Regeneration beyond the Glial Scar. *Nat. Rev. Neurosci.* 2004, 5 (2), 146-156.

(3) Ebinger, M.; Kunz, A.; Wendt, M.; Rozanski, M.; Winter, B.; Waldschmidt, C.; Weber, J.; Villringer, K.; Fiebach, J. B.; Audebert, H. J. Effects of Golden Hour Thrombolysis: A Prehospital Acute Neurological Treatment and Optimization of Medical Care in Stroke (PHANTOM-S) Substudy. *JAMA Neurol.* 2015, 72 (1), 25.

(4) Evaniew, N.; Belley-Côté, E. P.; Fallah, N.; Noonan, V. K.; Rivers, C. S.; Dvorak, M. F. Methylprednisolone for the Treatment of Patients with Acute Spinal Cord Injuries: A Systematic Review and Meta-Analysis. *J. Neurotrauma* 2016, 33 (5), 468-481.

(5) Bartlett, A. H.; Park, P. W. Proteoglycans in Host-Pathogen Interactions: Molecular Mechanisms and Therapeutic Implications. *Expert Rev. Mol. Med.* 2010, 12, e5.

(6) Garcia, B.; Merayo-Lloves, J.; Martin, C.; Alcalde, I.; Quirós, L. M.; Vazquez, F. Surface Proteoglycans as Mediators in Bacterial Pathogens Infections. *Front. Microbiol.* 2016, 7.

(7) Gill, S.; Wight, T. N.; Frevert, C. W. Proteoglycans: Key Regulators of Pulmonary Inflammation and the Innate Immune Response to Lung Infection. *Anat. Rec. Adv. Integr. Anat. Evol. Biol.* 2010, 293 (6), 968-981.

(8) Prabhakar, V.; Capila, I.; Bosques, C. J.; Pojasek, K.; Sasisekharan, R. Chondroitinase ABC I from *Proteus vulgaris*: Cloning, Recombinant Expression and Active Site Identification. *Biochem. J.* 2005, 386 (1), 103-112.

(9) Shaya, D.; Hahn, B.-S.; Bjerkan, T. M.; Kim, W. S.; Park, N. Y.; Sim, J.-S.; Kim, Y.-S.; Cygler, M. Composite Active Site of Chondroitin Lyase ABC Accepting Both Epimers of Uronic Acid. *Glycobiology* 2008, 18 (3), 270-277.

(10) Yamagata, T.; Saito, H.; Habuchi, O.; Suzuki, S. Purification and Properties of Bacterial Chondroitinases and Chondrosulfatases. *J. Biol. Chem.* 1968, 243 (7), 1523-1535.

(11) Hettiaratchi, M. H.; O'Meara, M. J.; Teal, C. J.; Payne, S. L.; Pickering, A. J.; Shoichet, M. S. Local Delivery of Stabilized Chondroitinase ABC Degrades Chondroitin Sulfate Proteoglycans in Stroke-Injured Rat Brains. *J. Controlled Release* 2019, 297, 14-25.
(12) Soleman, S.; Yip, P. K.; Duricki, D. A.; Moon, L. D. F. Delayed Treatment with Chondroitinase ABC Promotes Sensorimotor Recovery and Plasticity after Stroke in Aged Rats. *Brain* 2012, 135 (4), 1210-1223.
(13) Lin, R.; Kwok, J. C. F.; Crespo, D.; Fawcett, J. W. Chondroitinase ABC Has a Long-Lasting Effect on Chondroitin Sulphate Glycosaminoglycan Content in the Injured Rat Brain. *J. Neurochem.* 2007, 0 (0), 071116233414006-???
(14) Tennant, K. A. Thinking Outside the Brain: Structural Plasticity in the Spinal Cord Promotes Recovery from Cortical Stroke. *Exp. Neurol.* 2014, 254, 195-199.
(15) Warren, P. M.; Steiger, S. C.; Dick, T. E.; MacFarlane, P. M.; Alilain, W. J.; Silver, J. Rapid and Robust Restoration of Breathing Long after Spinal Cord Injury. *Nat. Commun.* 2018, 9 (1), 4843.
(16) Nori, S.; Khazaei, M.; Ahuja, C. S.; Yokota, K.; Ahlfors, J.-E.; Liu, Y.; Wang, J.; Shibata, S.; Chio, J.; Hettiaratchi, M. H.; et al. Human Oligodendrogenic Neural Progenitor Cells Delivered with Chondroitinase ABC Facilitate Functional Repair of Chronic Spinal Cord Injury. *Stem Cell Rep.* 2018, 11 (6), 1433-1448.
(17) Bradbury, E. J.; Moon, L. D.; Popat, R. J.; King, V. R.; Bennett, G. S.; Patel, P. N.; Fawcett, J. W.; McMahon, S. B. Chondroitinase ABC Promotes Functional Recovery after Spinal Cord Injury. *Nature* 2002, 416 (6881), 636.
(18) Garcia-Alias, G.; Barkhuysen, S.; Buckle, M.; Fawcett, J. W. Chondroitinase ABC Treatment Opens a Window of Opportunity for Task-Specific Rehabilitation. *Nat. Neurosci.* 2009, 12 (9), 1145.
(19) Rosenzweig, E. S.; Salegio, E. A.; Liang, J. J.; Weber, J. L.; Weinholtz, C. A.; Brock, J. H.; Moseanko, R.; Hawbecker, S.; Pender, R.; Cruzen, C. L. Chondroitinase Improves Anatomical and Functional Outcomes after Primate Spinal Cord Injury. *Nat. Neurosci.* 2019, 1.
(20) Tester, N. J.; Plaas, A. H.; Howland, D. R. Effect of Body Temperature on Chondroitinase ABC's Ability to Cleave Chondroitin Sulfate Glycosaminoglycans. *J Neurosci. Res.* 2007, 85 (5), 1110-1118.
(21) Harris, N. G.; Mironova, Y. A.; Hovda, D. A.; Sutton, R. L. Chondroitinase ABC Enhances Pericontusion Axonal Sprouting But Does Not Confer Robust Improvements in Behavioral Recovery. *J. Neurotrauma* 2010, 27 (11), 1971-1982.
(21a) Burnside, E. R.; De Winter, F.; Didangelos, A.; James, N. D.; Andreica, E-C.; Layard-Horsfall, H.; Muir, E. M.; Verhaagen, J.; Bradbury E. J. Immune-evasive gene switch enables regulated delivery of chondroitinase after spinal cord injury. *Brain* 2018, 141 (8), 2362-2381.
(22) Caggiano, A. O.; Iaci, J.; Vecchione, A.; Markensohn, E. Compositions and Methods of Using Chondroitinase ABCI Mutants. 2009.
(23) Nazari-Robati, M.; Khajeh, K.; Aminian, M.; Mollania, N.; Golestani, A. Enhancement of Thermal Stability of Chondroitinase ABC I by Site-Directed Mutagenesis: An Insight from Ramachandran Plot. Biochim. *Biophys. Acta BBA—Proteins Proteomics* 2013, 1834 (2), 479-486.
(24) Chen, Z.; Li, Y.; Feng, Y.; Chen, L.; Yuan, Q. Enzyme Activity Enhancement of Chondroitinase ABC I from *Proteus vulgaris* by Site-Directed Mutagenesis. *RSC Adv.* 2015, 5 (93), 76040-76047.
(25) Akram Shirdel, S.; Khalifeh, K.; Golestani, A.; Ranjbar, B.; Khajeh, K. Critical Role of a Loop at C-Terminal Domain on the Conformational Stability and Catalytic Efficiency of Chondroitinase ABC I. *Mol. Biotechnol.* 2015, 57 (8), 727-734.
(26) Shamsi, M.; Shirdel, S. A.; Jafarian, V.; Jafari, S. S.; Khalifeh, K.; Golestani, A. Optimization of Conformational Stability and Catalytic Efficiency in Chondroitinase ABC I by Protein Engineering Methods. *Eng. Life Sci.* 2016, 16 (8), 690-696.
(27) Kheirollahi, A.; Khajeh, K.; Golestani, A. Rigidifying Flexible Sites: An Approach to Improve Stability of Chondroitinase ABC I. *Int. J. Biol. Macromol.* 2017, 97, 270-278.
(28) Moradi, K.; Shirdel, S. A.; Shamsi, M.; Jafarian, V.; Khalifeh, K. Investigating the Structural and Functional Features of Representative Recombinants of Chondroitinase ABC I. *Enzyme Microb. Technol.* 2017, 107, 64-71.
(29) Shahaboddin, M. E.; Khajeh, K.; Maleki, M.; Golestani, A. Improvement of Activity and Stability of Chondroitinase ABC I by Introducing an Aromatic Cluster at the Surface of Protein. *Enzyme Microb. Technol.* 2017, 105, 38-44.
(30) Shahaboddin, M. E.; Khajeh, K.; Golestani, A. Establishment of Aromatic Pairs at the Surface of Chondroitinase ABC I: The Effect on Activity and Stability. *Appl. Biochem. Biotechnol.* 2018, 186 (2), 358-370.
(31) Maleki, M.; Khajeh, K.; Amanlou, M.; Golestani, A. Role of His-His Interaction in Ser474-His475-Tyr476 Sequence of Chondroitinase ABC I in the Enzyme Activity and Stability. *Int. J. Biol. Macromol.* 2018, 109, 941-949.
(32) Kheirollahi, A.; Khajeh, K.; Golestani, A. Investigating the Role of Loop 131-140 in Activity and Thermal Stability of Chondroitinase ABC I. *Int. J. Biol. Macromol.* 2018, 116, 811-816.
(33) Mohammadyari, H.; Shirdel, S. A.; Jafarian, V.; Khalifeh, K. Designing and Construction of Novel Variants of Chondroitinase ABC I to Reduce Aggregation Rate. *Arch. Biochem. Biophys.* 2019, 668, 46-53.
(34) Omidi-Ardali, H.; Aminian, M.; Golestani, A.; Shahaboddin, M. E.; Maleki, M. NA89 and CA274 Truncated Enzymes of Chondroitinase ABC I Regain More Imperturbable Microenvironments Around Structural Components in Comparison to Their Wild Type. *Protein J.* 2019, 38 (2), 151-159.
(35) Lee, H.; McKeon, R. J.; Bellamkonda, R. V. Sustained Delivery of Thermostabilized ChABC Enhances Axonal Sprouting and Functional Recovery after Spinal Cord Injury. *Proc. Natl. Acad. Sci.* 2010, 107 (8), 3340-3345.
(36) Nazari-Robati, M.; Khajeh, K.; Aminian, M.; Fathi-Roudsari, M.; Golestani, A. Co-Solvent Mediated Thermal Stabilization of Chondroitinase ABC I Form *Proteus vulgaris. Int. J. Biol. Macromol.* 2012, 50 (3), 487-492.
(37) Naderi, M. S.; Moghadam, T. T.; Khajeh, K.; Ranjbar, B. Improving the Stability of Chondroitinase ABC I via Interaction with Gold Nanorods. *Int. J. Biol. Macromol.* 2018, 107, 297-304.
(38) Askaripour, H.; Vossoughi, M.; Khajeh, K.; Alemzadeh, I. Magnetite Nanoparticle as a Support for Stabilization of Chondroitinase ABCI. *Artif Cells Nanomedicine Biotechnol.* 2019, 47 (1), 2721-2728.
(39) Fowler, D. M.; Araya, C. L.; Fleishman, S. J.; Kellogg, E. H.; Stephany, J. J.; Baker, D.; Fields, S. High-Resolution Mapping of Protein Sequence-Function Relationships. *Nat. Methods* 2010, 7 (9), 741-746.

(40) Goldenzweig, A.; Goldsmith, M.; Hill, S. E.; Gertman, O.; Laurino, P.; Ashani, Y.; Dym, O.; Unger, T.; Albeck, S.; Prilusky, J.; et al. Automated Structure- and Sequence-Based Design of Proteins for High Bacterial Expression and Stability. *Mol. Cell* 2016, 63 (2), 337-346.

(41) Musil, M.; Konegger, H.; Hon, J.; Bednar, D.; Damborsky, J. Computational Design of Stable and Soluble Biocatalysts. *ACS Catal.* 2019, 9 (2), 1033-1054.

(42) Lehmann, M.; Pasamontes, L.; Lassen, S. F.; Wyss, M. The Consensus Concept for Thermostability Engineering of Proteins. *Biochim. Biophys. Acta BBA—Protein Struct. Mol. Enzymol.* 2000, 1543 (2), 408-415.

(43) Kimura, M.; Ohta, T. On Some Principles Governing Molecular Evolution. *Proc. Natl. Acad. Sci.* 1974, 71 (7), 2848-2852.

(44) Akanuma, S.; Nakajima, Y.; Yokobori, S.; Kimura, M.; Nemoto, N.; Mase, T.; Miyazono, K.; Tanokura, M.; Yamagishi, A. Experimental Evidence for the Thermophilicity of Ancestral Life. *Proc. Natl. Acad. Sci.* 2013, 110 (27), 11067-11072.

(45) Huang, W.; Lunin, Vladimir V.; Li, Y.; Suzuki, S.; Sugiura, N.; Miyazono, H.; Cygler, M. Crystal Structure of *Proteus vulgaris* Chondroitin Sulfate ABC Lyase I at 1.9 Å Resolution. *J. Mol. Biol.* 2003, 328 (3), 623-634.

(46) Prabhakar, V.; Capila, I.; Raman, R.; Srinivasan, A.; Bosques, C. J.; Pojasek, K.; Wrick, M. A.; Sasisekharan, R. The Catalytic Machinery of Chondroitinase ABC I Utilizes a Calcium Coordination Strategy to Optimally Process Dermatan Sulfate†. *Biochemistry* 2006, 45 (37), 11130-11139.

(47) Loladze, V. V.; Ibarra-Molero, B.; Sanchez-Ruiz, J. M.; Makhatadze, G. I. Engineering a Thermostable Protein via Optimization of Charge-Charge Interactions on the Protein Surface†. *Biochemistry* 1999, 38 (50), 16419-16423.

(48) Matthews, B. W.; Nicholson, H.; Becktel, W. J. Enhanced Protein Thermostability from Site-Directed Mutations That Decrease the Entropy of Unfolding. *Proc. Natl. Acad. Sci.* 1987, 84 (19), 6663-6667.

(49) Zhao, H.; Arnold, F. H. Directed Evolution Converts Subtilisin E into a Functional Equivalent of Thermitase. *Protein Eng. Des. Sel.* 1999, 12 (1), 47-53.

(50) Pakulska, M. M.; Vulic, K.; Shoichet, M. S. Affinity-Based Release of Chondroitinase ABC from a Modified Methylcellulose Hydrogel. *J. Controlled Release* 2013, 171 (1), 11-16.

(51) Michel, G.; Pojasek, K.; Li, Y.; Sulea, T.; Linhardt, R. J.; Raman, R.; Prabhakar, V.; Sasisekharan, R.; Cygler, M. The Structure of Chondroitin B Lyase Complexed with Glycosaminoglycan Oligosaccharides Unravels a Calcium-Dependent Catalytic Machinery. *J. Biol. Chem.* 2004, 279 (31), 32882-32896.

(52) Li, H.-P.; Komuta, Y.; Kimura-Kuroda, J.; van Kuppevelt, T. H.; Kawano, H. Roles of Chondroitin Sulfate and Dermatan Sulfate in the Formation of a Lesion Scar and Axonal Regeneration after Traumatic Injury of the Mouse Brain. *J. Neurotrauma* 2013, 30 (5), 413-425.

(53) Vulic, K.; Shoichet, M. S. Tunable Growth Factor Delivery from Injectable Hydrogels for Tissue Engineering. *J. Am. Chem. Soc.* 2012, 134 (2), 882-885.

(54) Zuo, J.; Neubauer, D.; Dyess, K.; Ferguson, T. A.; Muir, D. Degradation of Chondroitin Sulfate Proteoglycan Enhances the Neurite-Promoting Potential of Spinal Cord Tissue. *Exp. Neurol.* 1998, 154 (2), 654-662.

(55) Corvetti, L.; Rossi, F. Degradation of Chondroitin Sulfate Proteoglycans Induces Sprouting of Intact Purkinje Axons in the Cerebellum of the Adult Rat. *J. Neurosci.* 2005, 25 (31), 7150-7158.

(1) Goldenzweig, A.; Goldsmith, M.; Hill, S. E.; Gertman, O.; Laurino, P.; Ashani, Y.; Dym, O.; Unger, T.; Albeck, S.; Prilusky, J.; et al. Automated Structure- and Sequence-Based Design of Proteins for High Bacterial Expression and Stability. *Mol. Cell* 2016, 63 (2), 337-346.

(2) Huang, W.; Lunin, VladimirV.; Li, Y.; Suzuki, S.; Sugiura, N.; Miyazono, H.; Cygler, M. Crystal Structure of *Proteus vulgaris* Chondroitin Sulfate ABC Lyase I at 1.9 Å Resolution. *J. Mol. Biol.* 2003, 328 (3), 623-634.

(3) Finn, R. D.; Coggill, P.; Eberhardt, R. Y.; Eddy, S. R.; Mistry, J.; Mitchell, A. L.; Potter, S. C.; Punta, M.; Qureshi, M.; Sangrador-Vegas, A.; et al. The Pfam Protein Families Database: Towards a More Sustainable Future. *Nucleic Acids Res.* 2016, 44 (D1), D279-D285.

(4) Altschul, S. F.; Madden, T. L.; Schaffer, A. A.; Zhang, J.; Zhang, Z.; Miller, W.; Lipman, D. J. Gapped BLAST and PSI-BLAST: A New Generation of Protein Database Search Programs. *Nucleic Acids Res.* 1997, 25 (17), 3389-3402.

(5) Edgar, R. C. MUSCLE: Multiple Sequence Alignment with High Accuracy and High Throughput. *Nucleic Acids Res.* 2004, 32 (5), 1792-1797.

(6) Kabsch, W.; Sander, C. Dictionary of Protein Secondary Structure: Pattern Recognition of Hydrogen-Bonded and Geometrical Features. *Biopolymers* 1983, 22 (12), 2577-2637.

(7) Altschul, S. F.; Gish, W.; Miller, W.; Myers, E. W.; Lipman, D. *J. Basic* Local Alignment Search Tool. *J. Mol. Biol.* 1990, 215 (3), 403-410.

(8) Whitehead, T. A.; Chevalier, A.; Song, Y.; Dreyfus, C.; Fleishman, S. J.; De Mattos, C.; Myers, C. A.; Kamisetty, H.; Blair, P.; Wilson, I. A.; et al. Optimization of Affinity, Specificity and Function of Designed Influenza Inhibitors Using Deep Sequencing. *Nat. Biotechnol.* 2012, 30 (6), 543-548.

(9) Pakulska, M. M.; Vulic, K.; Shoichet, M. S. Affinity-Based Release of Chondroitinase ABC from a Modified Methylcellulose Hydrogel. *J. Controlled Release* 2013, 171 (1), 11-16.

(10) Whitmore, L.; Wallace, B. A. DICHROWEB, an Online Server for Protein Secondary Structure Analyses from Circular Dichroism Spectroscopic Data. *Nucleic Acids Res.* 2004, 32 (Web Server), W668-W673.

(11) Kheirollahi, A.; Khajeh, K.; Golestani, A. Rigidifying Flexible Sites: An Approach to Improve Stability of Chondroitinase ABC I. *Int. J. Biol. Macromol.* 2017, 97, 270-278.

(12) Pakulska, M. M.; Tator, C. H.; Shoichet, M. S. Local Delivery of Chondroitinase ABC with or without Stromal Cell-Derived Factor 1α Promotes Functional Repair in the Injured Rat Spinal Cord. *Biomaterials* 2017, 134, 13-21.

(13) Hettiaratchi, M. H.; O'Meara, M. J.; Teal, C. J.; Payne, S. L.; Pickering, A. J.; Shoichet, M. S. Local Delivery of Stabilized Chondroitinase ABC Degrades Chondroitin Sulfate Proteoglycans in Stroke-Injured Rat Brains. *J. Controlled Release* 2019, 297, 14-25.

(14) Bodenhofer, U.; Bonatesta, E.; Horejs-Kainrath, C.; Hochreiter, S. Msa: An R Package for Multiple Sequence Alignment. *Bioinformatics* 2015, btv494.

(15) Cleveland, W. S.; Loader, C. Smoothing by Local Regression: Principles and Methods. In *Statistical theory and computational aspects of smoothing*; Springer, 1996; pp 10-49.

(16) El-Gebali, S.; Mistry, J.; Bateman, A.; Eddy, S. R.; Luciani, A.; Potter, S. C.; Qureshi, M.; Richardson, L. J.; Salazar, G. A.; Smart, A.; et al. The Pfam Protein Families Database in 2019. *Nucleic Acids Res.* 2019, 47 (D1), D427-D432.

(17) Wickham, H. Ggplot2: Elegant Graphics for Data Analysis; Springer, 2016.

(18) Schrodinger, L. The PyMOL Molecular Graphics System. 2010. *Version* 2019, 1, rl.

(19) Madeira, F.; Park, Y. mi; Lee, J.; Buso, N.; Gur, T.; Madhusoodanan, N.; Basutkar, P.; Tivey, A. R. N.; Potter, S. C.; Finn, R. D.; et al. The EMBL-EBI Search and Sequence Analysis Tools APIs in 2019. *Nucleic Acids Res.* 2019, 47 (W1), W636-W641.

(20) Rambaut, A. FigTree v1. 4.2, a Graphical Viewer of Phylogenetic Trees. 2014. 2018.

(21) Kamisetty, H.; Ovchinnikov, S.; Baker, D. Assessing the Utility of Coevolution-Based Residue-Residue Contact Predictions in a Sequence- and Structure-Rich Era. *Proc. Natl. Acad. Sci.* 2013, 110 (39), 15674-15679.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A mutant of a wild-type chondroitinase ABC (ChABC), wherein the mutant has ChABC activity, a melting temperature that is at least 4° C. higher than the melting temperature of the wild-type ChABC, and a functional half-life that is at least 4 times longer than that of the wild-type ChABC, wherein the mutant comprises at least 15 point mutations in domain 2 of the wild-type ChABC, wherein:

the wild-type ChABC comprises the amino acid sequence of SEQ ID NO:1 or an amino acid sequence that is homologous to the amino acid sequence of SEQ ID NO:1, wherein when the homologous amino acid sequence is aligned with the sequence of SEQ ID NO:1 it has a BLAST expectation value of less than $1e^{-50}$; and domain 2 consists of amino acid residues 243-604 of SEQ ID NO:1 or amino acid residues corresponding to amino acid residues 243-604 of SEQ ID NO:1 in the homologous amino acid sequence, wherein the mutations in domain 2 are:

substitutions in the amino acid sequence of SEQ ID NO:1 selected from the group consisting of K244E, Q246L, L247P, V249A, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, V470L, N471H, S517A, S529E, N536Q, K583P, S592A, A596R, and D599G; or substitutions in the homologous amino acid sequence selected from the group consisting of substitutions corresponding with K244E, Q246L, L247P, V249A, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, V470L, N471H, S517A, S529E, N536Q, K583P, S592A, A596R, and D599G in SEQ ID NO:1.

2. The mutant of claim 1, wherein the mutant comprises at least 18 point mutations in domain 2 of the wild-type ChABC.

3. The mutant of claim 1, wherein the mutant comprises from 15 to 40 point mutations in domain 2 of the wild-type ChABC.

4. The mutant of claim 1, wherein the mutant further comprises at least 5 point mutations in domain 3 of the wild-type enzyme, wherein domain 3 consists of amino acid residues 623-882 of SEQ ID NO:1 or amino acid residues corresponding to amino acid residues 623-882 of SEQ ID NO:1 in the homologous amino acid sequence.

5. The mutant of claim 4, wherein the mutant comprises from 5 to 35 point mutations in domain 3 of the wild-type enzyme.

6. The mutant of claim 1, wherein the mutant has an amino acid sequence comprising (a) the following 18 substitutions:

K244E, I257V, A278K, L308I, I314K, N321H, S324P, N338D, S347A, E353N, S393N, T401A, A438P, K465E, V470L, N471H, S517A, and K583P, based on the amino acid sequence of SEQ ID NO:1, or substitutions in the homologous amino acid sequence that correspond with K244E, I257V, A278K, L308I, I314K, N321H, S324P, N338D, S347A, E353N, S393N, T401A, A438P, K465E, V470L, N471H, S517A, and K583P in the amino acid sequence of SEQ ID NO:1; or (b) the following 23 mutations:

K244E, Q246 μL, V249A, I257V, A278K, L308I, I314K, N321H, S324P, N338D, S347A, E353N, S393N, T401A, S437G, A438P, K465E, V470L, N471H, S517A, N536Q, K583P, and A596R, based on the amino acid sequence of SEQ ID NO:1, or substitutions in the homologous amino acid sequence that correspond with substitutions K244E, Q246 μL, V249A, I257V, A278K, L308I, I314K, N321H, S324P, N338D, S347A, E353N, S393N, T401A, S437G, A438P, K465E, V470L, N471H, S517A, N536Q, K583P, and A596R in the amino acid sequence of SEQ ID NO:1; or (c) the following 34 mutations:

K244E, Q246L, L247P, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, N471H, S517A, S529E, N536Q, K583P, S592A, A596R, and D599G, based on the amino acid sequence of SEQ ID NO:1, or substitutions in the homologous amino acid sequence that correspond with K244E, Q246L, L247P, I257V, L259T, N266D, V269A, A278K, S284D, D289K, N300D, L308I, I314K, N321H, S324P, N338D, S347A, V351Y, E353N, S393N, T401A, T415Q, S437G, A438P, D442N, K465E, N471H, S517A, S529E, N536Q, K583P, S592A, A596R, and D599G, in the amino acid sequence of SEQ ID NO:1.

7. The mutant of claim 4, wherein the mutations in domain 3 are:

substitutions in the amino acid sequence of SEQ ID NO:1 selected from the group consisting of Q636G, A644G, T647K, N656T, N656H, V669T, N675Y, L679K, Q685E, Q686N, E694P, K704D, K704E, D705E, K710N, R720T, I740Q, A743Q, E746P, K779Y, E805T, N806Q, N806T, Q814T, Q814G, Q831E, V843T, E846D, T866R and D870N; or substitutions in the homologous amino acid sequence selected from the group consisting of substitutions corresponding with Q636G, A644G, T647K, N656T, N656H, V669T, N675Y, L679K, Q685E, Q686N, E694P, K704D, K704E, D705E, K710N, R720T, I740Q, A743Q, E746P, K779Y, E805T, N806Q, N806T, Q814T, Q814G, Q831E, V843T, E846D, T866R and D870N in SEQ ID NO:1.

8. The mutant of claim 7, wherein the mutant has an amino acid sequence comprising:

(a) the following 7 mutations:

N656H, N675Y, Q685E, E694P, K704D, R720T, and Q831E, based on the amino acid sequence of SEQ ID NO:1, or substitutions in the homologous amino acid sequence that correspond with N656H, N675Y, Q685E, E694P, K704D, R720T, and Q831E in the amino acid sequence of SEQ ID NO:1;

(b) the following 12 mutations:

A644G, N656T, N675Y, Q685E, E694P, K704D, K710N, R720T, N806T, Q814T, Q831E, and T866R, based on the amino acid sequence of SEQ ID NO:1, or substitutions in the homologous amino acid sequence that correspond with A644G, N656T, N675Y, Q685E, E694P, K704D, K710N, R720T, N806T, Q814T, Q831E, and T866R in the amino acid sequence of SEQ ID NO:1; or (c) the following 26 mutations:

Q636G, A644G, T647K, N656T, V669T, N675Y, L679K, Q685E, Q686N, E694P, K704E, D705E, K710N, R720T, 1740Q, A743Q, E746P, K779Y, E805T, N806Q, Q814G, Q831E, V843T, E846D, T866R and D870N, based on the amino acid sequence of SEQ ID NO:1, or substitutions in the homologous amino acid sequence that correspond with Q636G, A644G, T647K, N656T, V669T, N675Y, L679K, Q685E, Q686N, E694P, K704E, D705E, K710N, R720T, 1740Q, A743Q, E746P, K779Y, E805T, N806Q, Q814G, Q831E, V843T, E846D, T866R and D870N in the amino acid sequence of SEQ ID NO: 1.

9. The mutant of claim 1, wherein the mutant comprises the amino acid sequence of SEQ ID NO: 2, SEQ ID NO: 3, SEQ ID NO:4, or a conservative variant thereof.

10. A fusion protein comprising the mutant of claim 1 and a binding peptide.

11. The fusion protein of claim 10, wherein the binding peptide is a Src Homology 3 (SH3) domain.

12. A polynucleotide comprising a nucleic acid sequence encoding the mutant of claim 1 or a fusion protein thereof, wherein the fusion protein comprises a binding peptide.

13. A vector comprising the nucleic acid molecule of claim 12.

14. A host cell comprising the polynucleotide of claim 12.

15. A process for producing or expressing the mutant of claim 1 or a fusion protein thereof, wherein the fusion protein comprises a binding peptide and the process comprises the steps of:

a) transforming or transfecting a host cell with a vector comprising a nucleic acid sequence encoding the mutant of claim 1;

b) culturing the host cell under conditions which allow the expression of the mutant or the fusion protein; and, optionally, c) isolating the mutant or the fusion protein.

16. A method for degrading proteoglycans in a subject in need thereof, comprising administering the mutant of claim 1 to the subject.

17. The method of claim 16, wherein degrading the proteoglycans promotes nerve regeneration in the subject.

18. The method of claim 16, wherein the method is for treating a cancer, a central nervous system injury, a spinal cord injury, a neurodegenerative disorder, a stroke scarring, or a fibrosis disease that involves a chondroitin sulfate (CS) or dermatan sulfate (DS) deposition in the subject, wherein the fibrosis disease that involves the CS or DS deposition comprises a cardiac fibrosis, a pulmonary fibrosis, or a fibrotic renal disease.

19. An in vitro method for degrading proteoglycans or analyzing proteoglycans, wherein the in vitro method comprises the step of contacting a sample comprising the proteoglycans with the mutant of claim 1.

20. A pharmaceutical composition comprising the mutant of claim 1, and a pharmaceutically acceptable diluent or excipient.

* * * * *